(12) United States Patent
Reddy et al.

(10) Patent No.: US 9,505,733 B2
(45) Date of Patent: *Nov. 29, 2016

(54) SINGLE STEP ENANTIOSELECTIVE PROCESS FOR THE PREPARATION OF 3-SUBSTITUTED CHIRAL PHTHALIDES

(71) Applicant: Council of Scientific & Industrial Research, New Delhi (IN)

(72) Inventors: Rekula Santosh Reddy, Pune (IN); Chithanya Kiran Indukuru Naga, Pune (IN); Sudalai Arumugam, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/694,588

(22) Filed: Apr. 23, 2015

(65) Prior Publication Data

US 2015/0299154 A1 Oct. 22, 2015

Related U.S. Application Data

(62) Division of application No. 14/357,952, filed as application No. PCT/IB2012/056340 on Nov. 12, 2012, now Pat. No. 9,073,887.

(30) Foreign Application Priority Data

Nov. 18, 2011 (IN) ............................ 3287/DEL/2011

(51) Int. Cl.
| C07D 311/82 | (2006.01) |
| C07D 307/88 | (2006.01) |
| C07B 53/00 | (2006.01) |
| C07D 307/92 | (2006.01) |
| C07D 493/04 | (2006.01) |

(52) U.S. Cl.
CPC ............. *C07D 307/88* (2013.01); *C07B 53/00* (2013.01); *C07D 307/92* (2013.01); *C07D 493/04* (2013.01)

(58) Field of Classification Search
CPC .................................................... C07D 307/88
USPC ......................................................... 549/305
See application file for complete search history.

(56) References Cited

PUBLICATIONS

Schwaben et al. Synthesis, (18), 2929-2934; 2011.*
Ozheki et al. Biosci. Biotechnol. Biochem., 67 (10), 2240-2244, 2003.*
Dorwald, "Side Reactions in Organic Synthesis," Wiley-VCH Verlag GmbH & Co. KGaA, 2005.
US Notice of Allowance dated Feb. 23, 2015 issued in U.S. Appl. No. 14/357,952.
US Office Action dated Nov. 6, 2014 issued in U.S. Appl. No. 14/357,952.

* cited by examiner

*Primary Examiner* — Nizal Chandrakumar
(74) *Attorney, Agent, or Firm* — Foley & Lardner LLP

(57) ABSTRACT

The present invention discloses single step, highly enantioselective catalytic oxidative cyclization process for the synthesis of 3-substituted chiral phthalides. In particular, the invention discloses asymmetric synthesis of chiral phthalides via synergetic nitrile accelerated oxidative cyclization of o-cyano substituted aryl alkenes in high yield and enantiomeric excess (ee) in short reaction time. Also, disclosed herein is "one-pot" asymmetric synthesis of biologically important natural compounds having 3-substituted chiral phthalide structural framework in the molecule.

3 Claims, 10 Drawing Sheets

Fig 1 COSY of II a
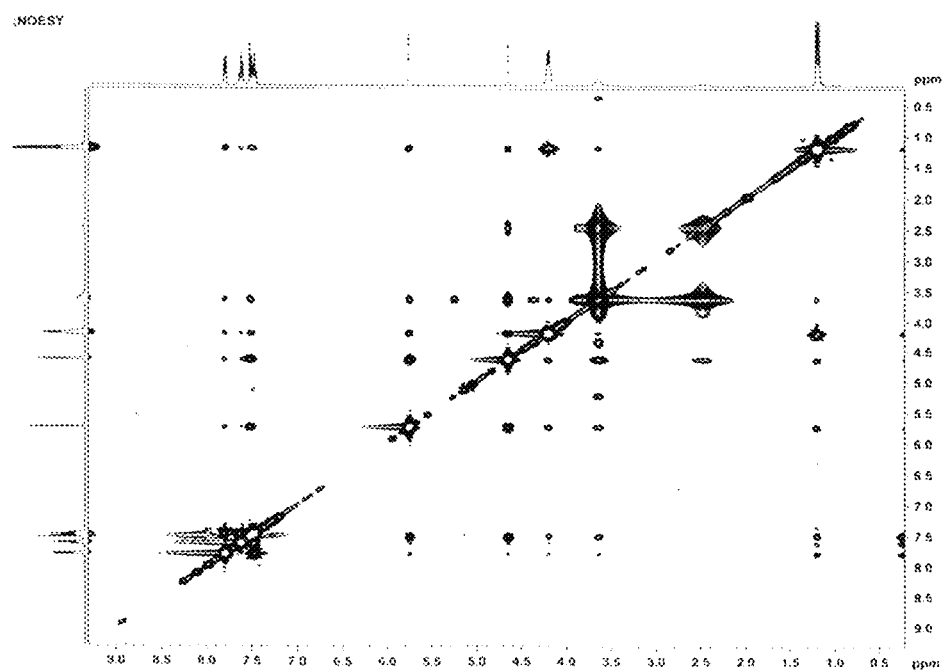
Fig 2 HSQCGP of II a
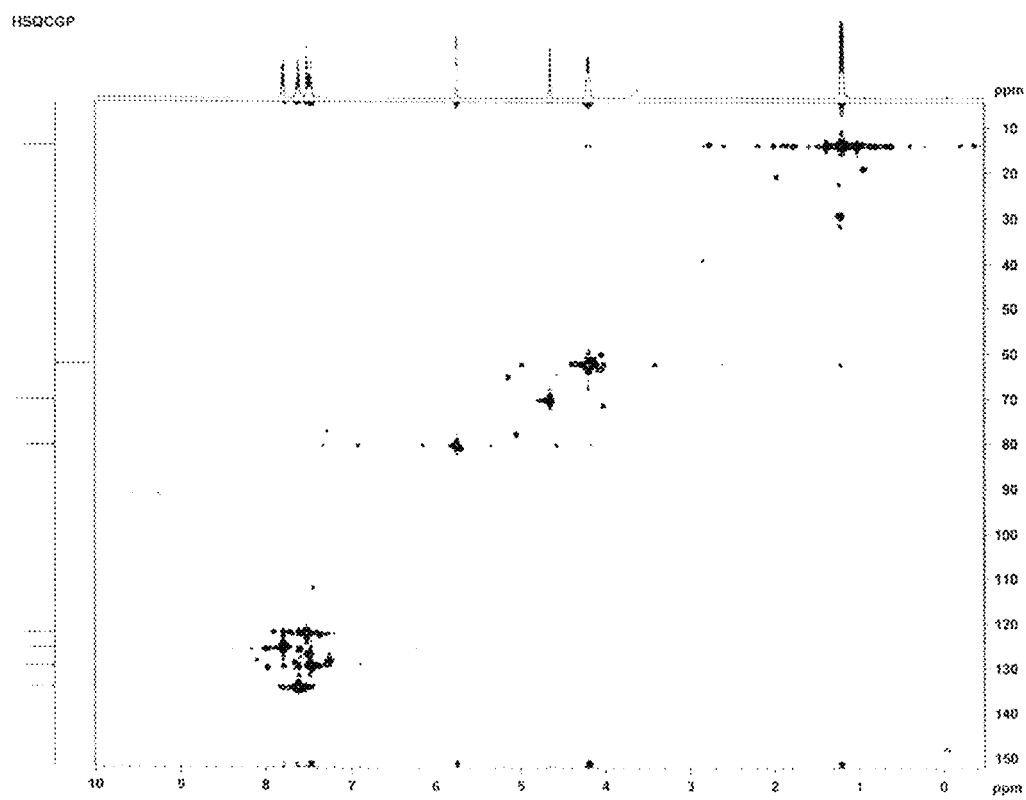

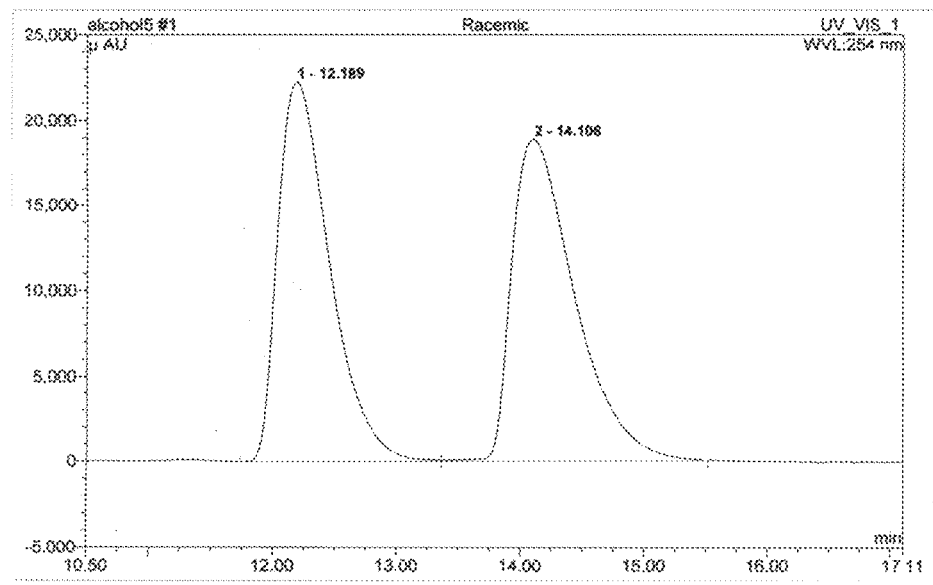
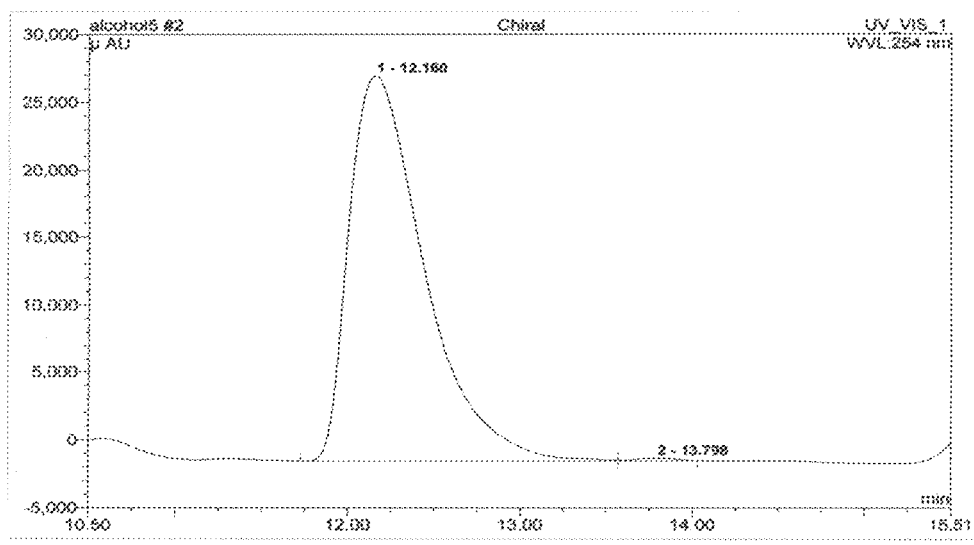
| No | Ret. Time | Height | Area | Rel. Area | Amount | Type |
|---|---|---|---|---|---|---|
| | min | μAU | μAU* min | % | | |
| 1 | 12.16 | 28495.075 | 14410.126 | 99.65 | n. a. | BMB |
| 2 | 13.80 | 189.662 | 50.523 | 0.35 | n. a. | BMB |
Fig 3 HPLC chromatogram of II a

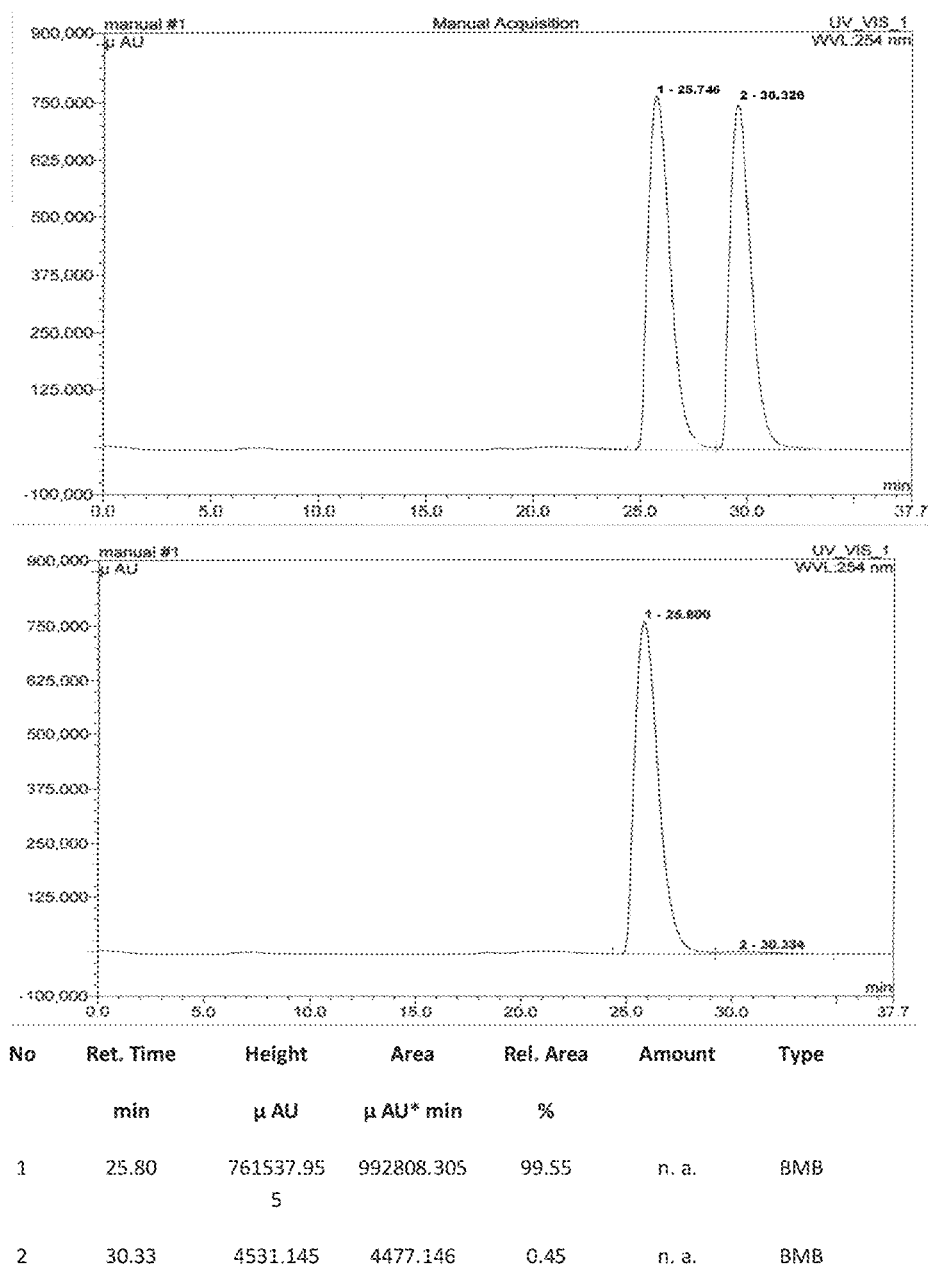
Fig 4 HPLC chromatogram of II b

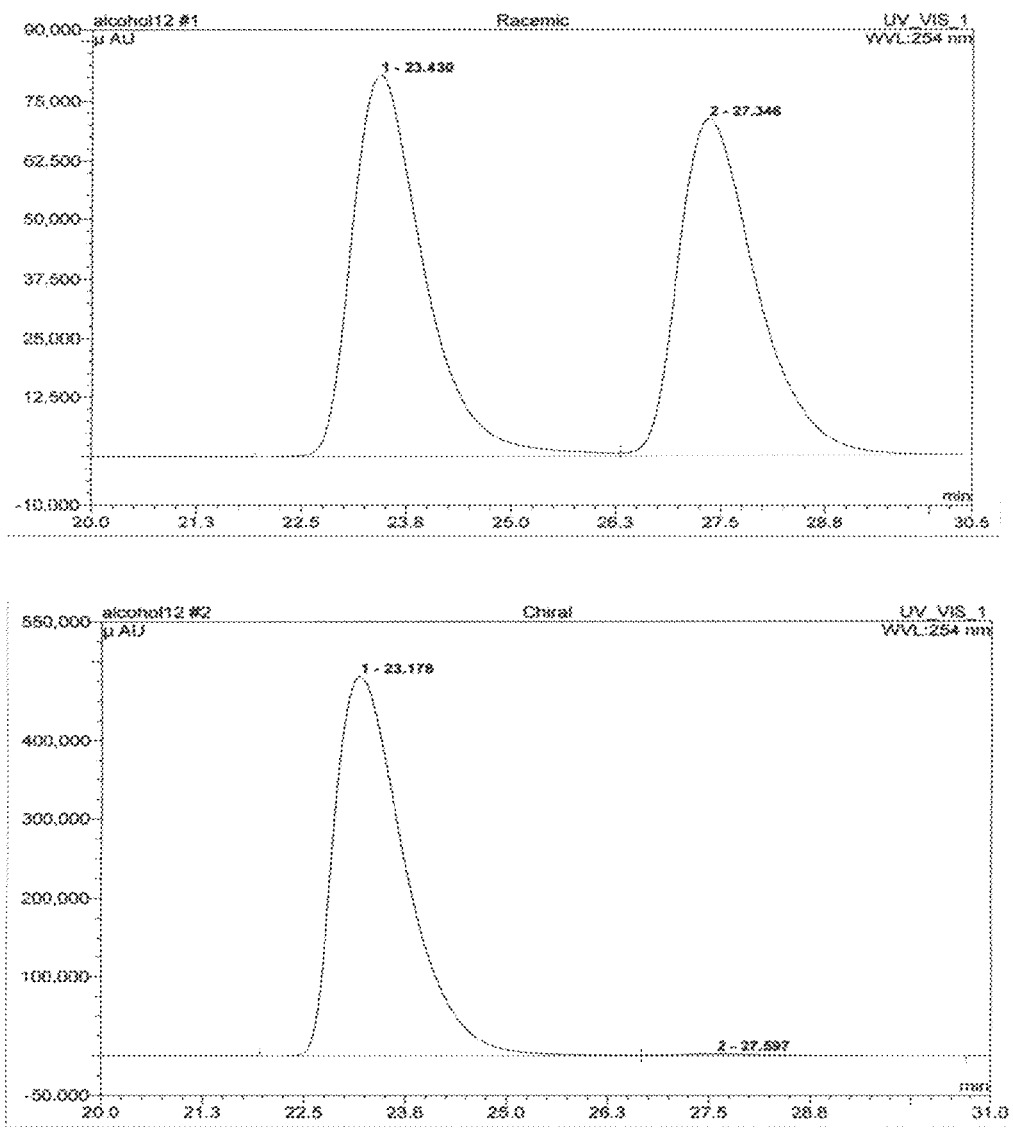
Fig 5 HPLC chromatogram of II c

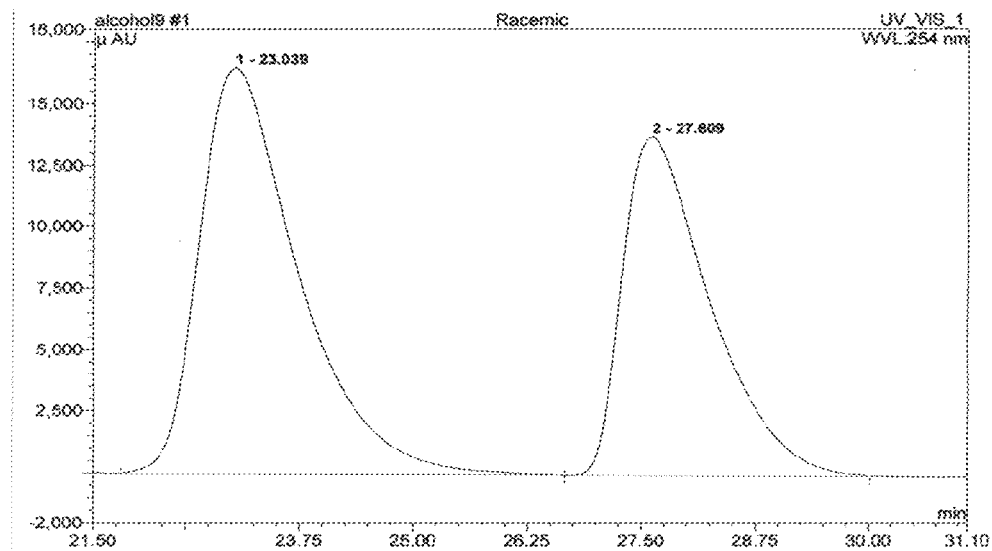
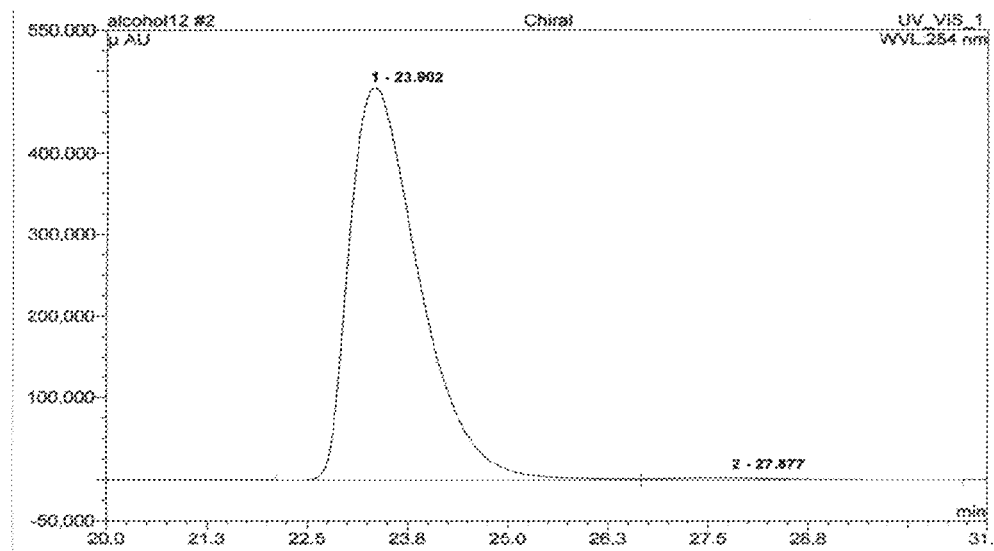
| No | Ret. Time | Height | Area | Rel. Area | Amount | Type |
|---|---|---|---|---|---|---|
|  | min | µAU | µAU* min | % |  |  |
| 1 | 23.90 | 48072.355 | 484390.220 | 99.44 | n. a. | BMB |
| 2 | 27.87 | 2273.930 | 3113.222 | 0.56 | n. a. | BMB |
Fig 6 HPLC chromatogram of II d

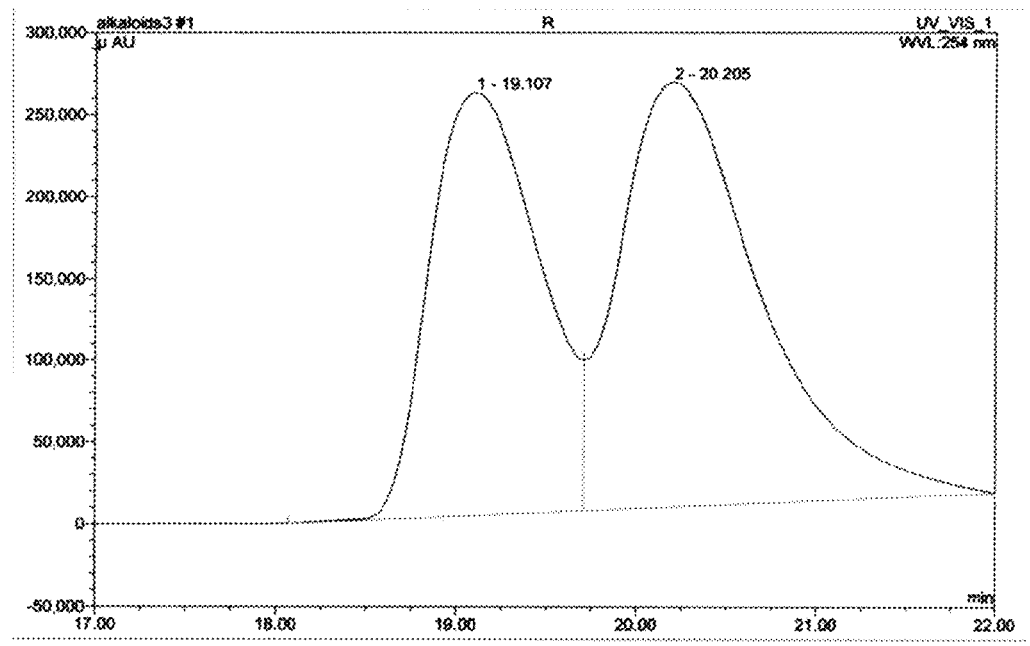
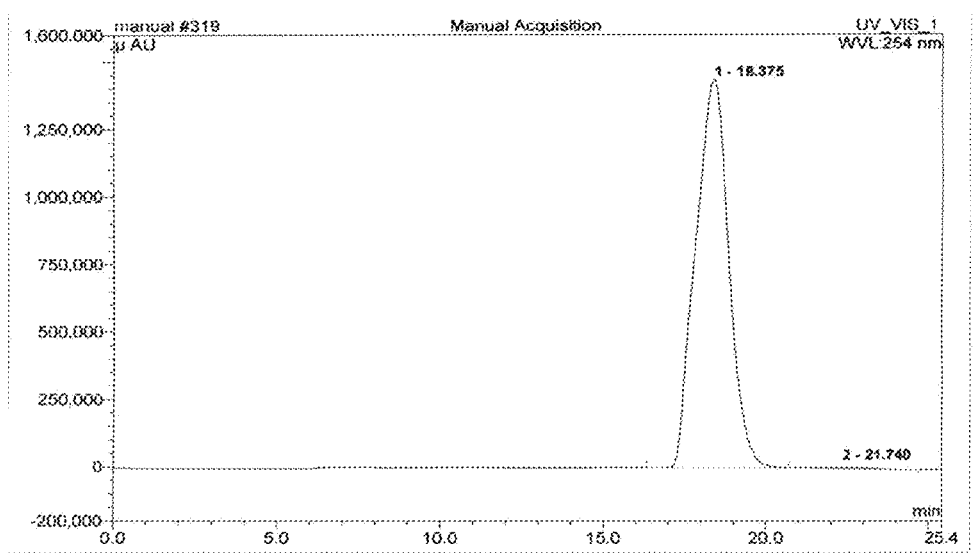
| No | Ret. Time | Height | Area | Rel. Area | Amount | Type |
|---|---|---|---|---|---|---|
| | min | μAU | μAU* min | % | | |
| 1 | 18.37 | 1436573.591 | 1817973.860 | 99.60 | n. a. | BMB |
| 2 | 21.74 | 106560.833 | 7299.549 | 0.40 | n. a. | BMB |
Fig 7 HPLC chromatogram of II e

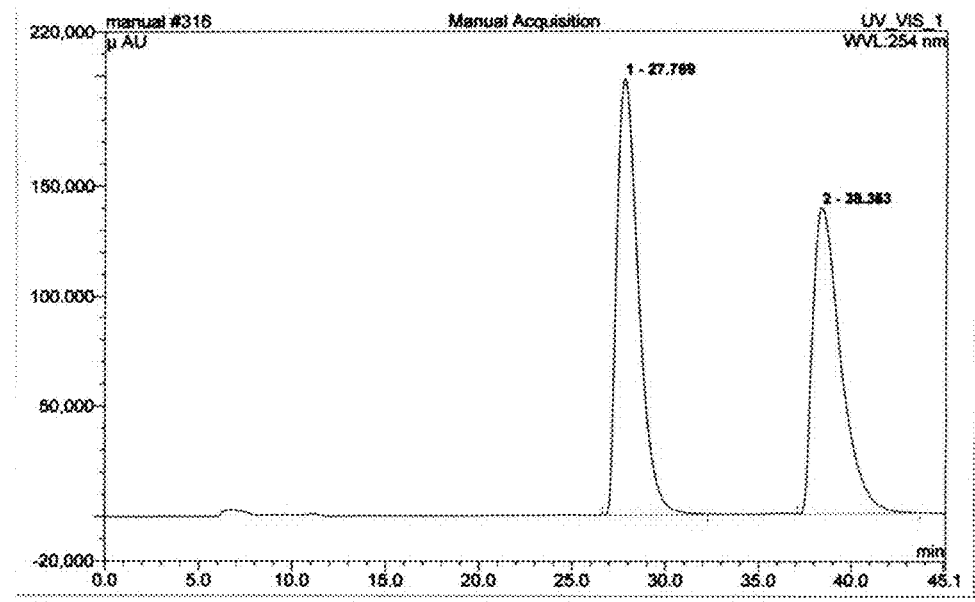
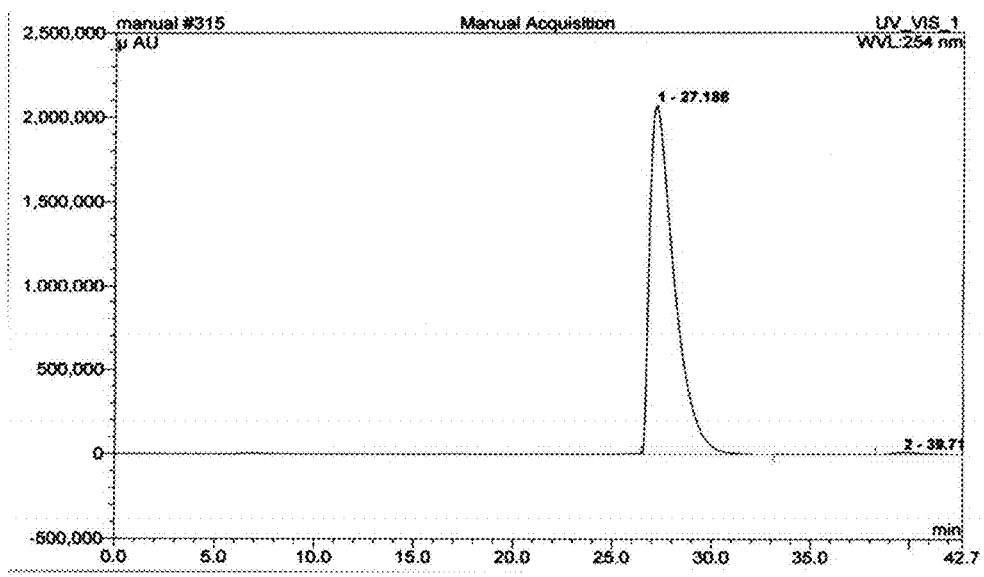
| No | Ret. Time | Height | Area | Rel. Area | Amount | Type |
|---|---|---|---|---|---|---|
|  | min | μ AU | μ AU* min | % |  |  |
| 1 | 27.19 | 2066521.172 | 26133.285 | 99.36 | n. a. | BMB |
| 2 | 39.72 | 10209.799 | 168.309 | 0.64 | n. a. | BMB |
Fig 8 HPLC chromatogram of II n

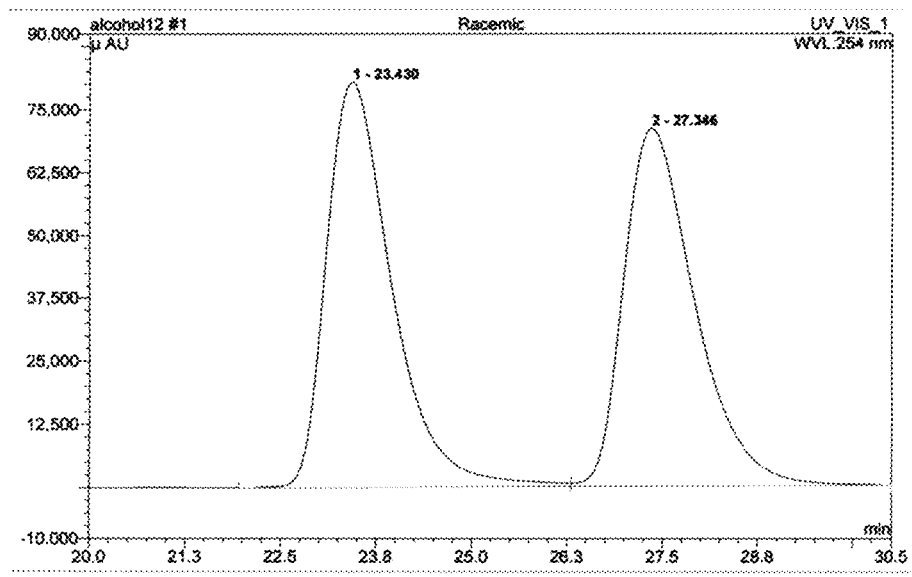
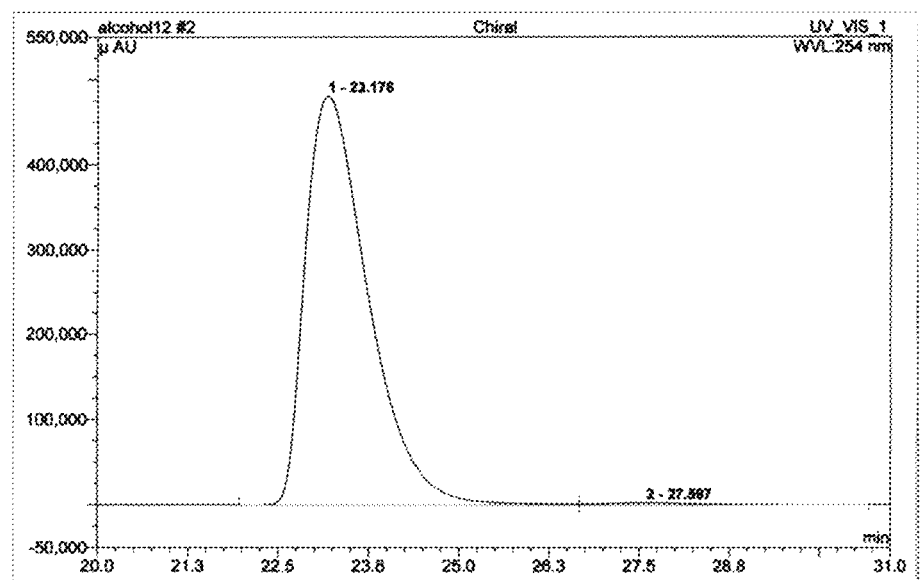
| No | Ret. Time | Height | Area | Rel. Area | Amount | Type |
|---|---|---|---|---|---|---|
| | min | µAU | µAU* min | % | | |
| 1 | 23.18 | 480683.355 | 484381.220 | 99.36 | n. a. | BMB |
| 2 | 27.60 | 2265.930 | 3105.222 | 0.64 | n. a. | BMB |
Fig 9 HPLC chromatogram of II o

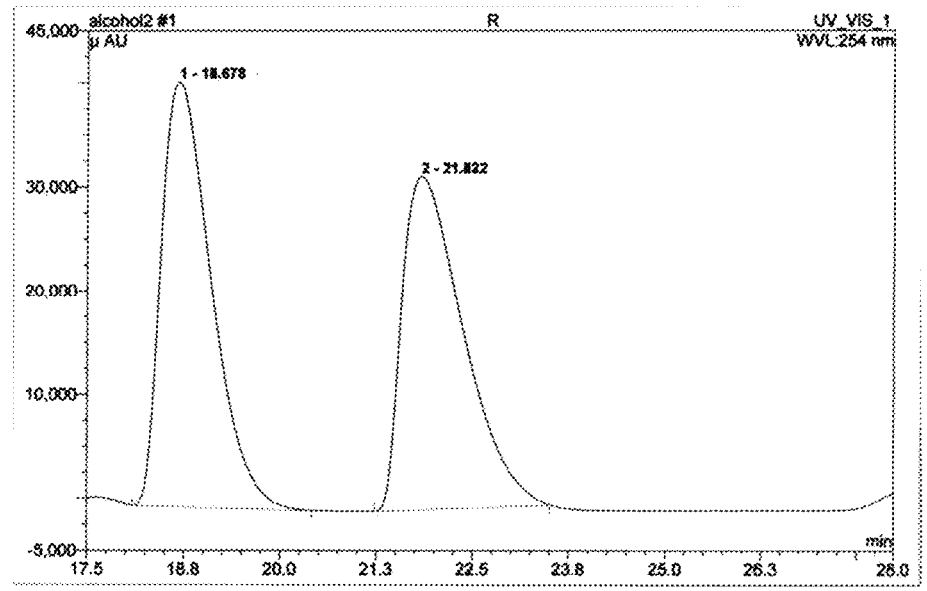
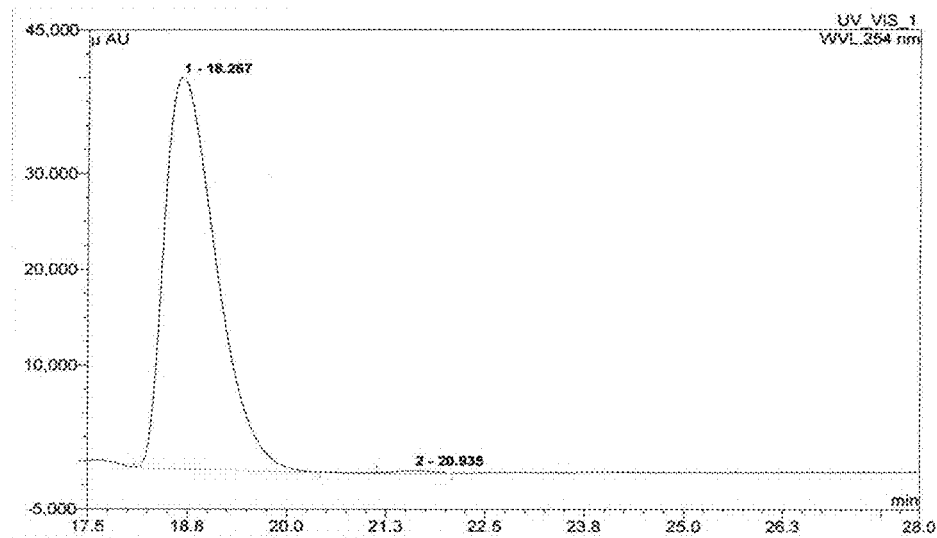
| No | Ret. Time | Height | Area | Rel. Area | Amount | Type |
|---|---|---|---|---|---|---|
| | min | µ AU | µ AU* min | % | | |
| 1 | 18.27 | 40869.477 | 30535.089 | 99.36 | n. a. | BMB |
| 2 | 20.93 | 2265.930 | 196.683 | 0.64 | n. a. | BMB |
Fig 10 HPLC chromatogram of II p

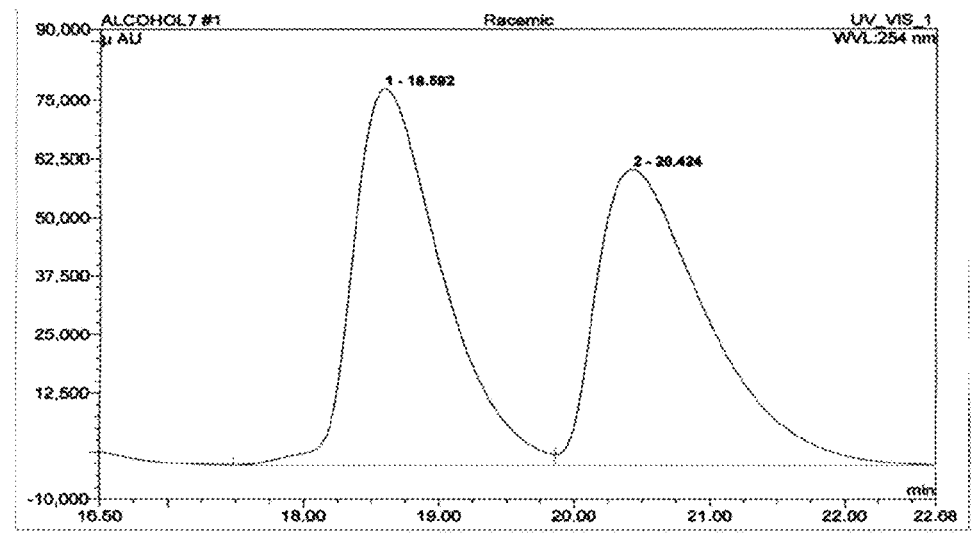
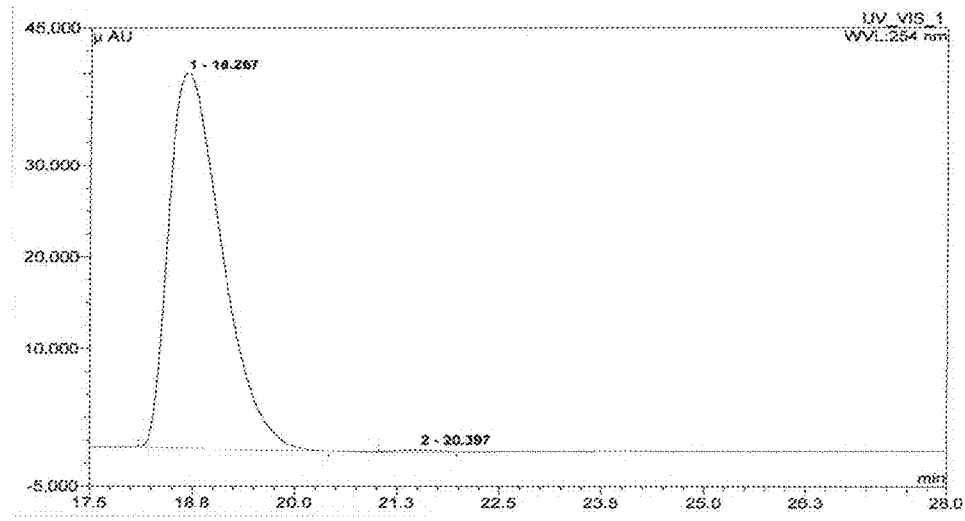
| No | Ret. Time | Height | Area | Rel. Area | Amount | Type |
|---|---|---|---|---|---|---|
| | min | µ AU | µ AU* min | % | | |
| 1 | 18.27 | 40895.238 | 30456.124 | 99.36 | n. a. | BMB |
| 2 | 20.40 | 2196.930 | 195.138 | 0.64 | n. a. | BMB |
Fig 11 HPLC chromatogram of II q

SINGLE STEP ENANTIOSELECTIVE PROCESS FOR THE PREPARATION OF 3-SUBSTITUTED CHIRAL PHTHALIDES

The following specification particularly describes the invention and the manner in which it is to be performed:

FIELD OF INVENTION

The present invention relates to a single step, highly enantioselective catalytic oxidative cyclization process for the synthesis of 3-substituted chiral phthalides. In particular, the invention relates to asymmetric synthesis of chiral phthalides via synergetic nitrile accelerated oxidative cyclization of o-cyano substituted aryl alkenes in high yield and enantiomeric excess (ee) in short reaction time. The present invention further relates to "one-pot" asymmetric synthesis of biologically important natural compounds having 3-substituted chiral phthalide structural framework in the molecule.

BACKGROUND OF THE INVENTION

Chiral phthalides [isobenzofuran-1(3H)-ones] comprising of 5-membered lactones are found in large number of plant products with broad and potent biological activities. An article titled "The Structural Diversity of Phthalides from the Apiaceae" by John J. Beck in J. Nat. Prod., 2007, 70 (5), pp 891-900 discloses the bioactivity of chiral phthalides against several illnesses and physiological conditions, including microbial and viral infections, stroke, tuberculosis.

Due to the biological importance of the 3-substituted chiral phthalides, their molecular architectures have become a platform for new synthetic methodology development. Over the past two decades, a variety of methods toward introducing C-3 chirality in phthalides have been established which include i) transfer hydrogenation of ketone [*Tetrahedron Lett.* 1990, 31, 5509 by Noyori et al]. ii) catalytic enantioselective addition of dialkylzinc reagents to o-phthalaldehyde [*J. Org. Chem.* 1992, 57, 742 by Butsugan et al]. iii) Nickel-catalyzed tandem reaction to asymmetric synthesis of chiral phthalides [*Synlett* 2002, 927 by Lin et al]. iv) enantioselective cross alkyne cyclotrimerization in the presence of the cationic complex [$Rh^I${(S)—$H_8$-binap} [*Angew. Chem., Int. Ed.* 2004, 43, 6510] and rhodium-catalyzed asymmetric one-pot transesterification and [2+2+2] cycloaddition disclosed in M. *Org. Lett.* 2007, 9, 1307 by Tanaka et al vi) alkynylation of aldehydes (Trost, B. M.; Weiss, A. H. *Angew. Chem., Int. Ed.* 2007, 46, 7664.), (vii) cyclization approach (Chang, H. T.; Jaganmohan, M.; Cheng, C. H. *Chem. Eur. J.* 2007, 13, 4356), (viii) organocatalytic aldol-lactonization process (Zhang, H.; Zhang, S.; Liu, L.; Luo, G.; Duan, W.; Wang. W. *J. Org. Chem.* 2010, 75, 368.) and reductive cyclization of 2-acylarylcarboxylates (Zhang, B.; Xu, M. H.; Lin G. Q. *Org. Lett.* 2009, 11, 4712).

Ligand accelerated Sharpless Asymmetric Dihydroxylation (AD) of prochiral olefins is widely used for the generation of 1,2-diols. Enantioselectivity is achieved through the addition of enantiomerically-enriched chiral ligands [(DHQD)2PHAL, (DHQ)2PHAL or their derivatives] which are available as prepackaged mixtures (AD-mix α and AD-mix β, AD=asymmetric dihydroxylation) for either enantiopreference. The present inventors in their earlier studies have reported a method that employs AD process followed by Co-catalyzed "one-pot" reductive cyclization ($CoCl_2$—$NaBH_4$) of nitro cyclic sulfites, which led to the construction of 3-substituted tetrahydroquinolin-3-ols.

Further, the said process was extended to prepare synthetically useful benzazepines i.e via AD process and catalytically accelerated reductive cyclisation of cyano cyclic sulfites.

In view of the biological importance of 3-substituted chiral phthalides and the limitations envisaged in the prior art processes for preparation of the same, the inventors of present invention believed that AD process followed by catalytic oxidative cyclisation could provide 3-substituted chiral phthalides in high yield and optical purity in short time.

However, the aforesaid processes employ chiral auxiliaries and expensive organometallic reagents that lack broad substrate scope and higher reaction stereo selectivity, also very few process are catalytic and atom economical.

OBJECTIVE OF THE PRESENT INVENTION

The main object of the present invention is to provide highly enantioselective, single step, catalytic oxidative cyclization method for the synthesis of 3-substituted chiral phthalides and their structural analogues via Asymmetric Dihydroxylation (AD) process of o-cyano substituted aryl alkenes with high yield and 99% ee in short reaction time.

Another object of the present invention is to provide a single step, enantioselective process which is easy to perform, energy saving, ecofriendly, atom economic reaction generating relatively less effluents.

SUMMARY OF THE INVENTION

Accordingly, the present invention provides single step, asymmetric dihydroxylation (AD) and nitrile accelerated catalytic oxidative cyclization for synthesis of 3-substituted chiral phthalides of Formula II, comprising, reacting o-cyano substituted aryl alkenes of Formula I with AD-mix-β in presence of a solvent at room temperature ranging between 25-35° C. for a period ranging between 3-7 h

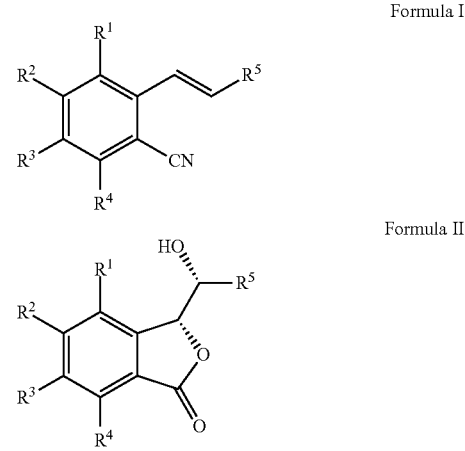

Formula I

Formula II wherein, R1, R2, R3 and R4 are independently same or different groups selected from hydrogen, C1-C7 straight or branched alkyl (optionally substituted with halo, hydroxyl, nitro, alkoxy, amido, nitrile, amine), C2-C7 straight or branched alkenyl (optionally substituted with halo, hydroxyl, nitro, alkoxy, amido, nitrile, amine), C2-C7 straight or branched alkynyls (optionally substituted with halo, hydroxyl, nitro, alkoxy, amido, nitrile, amine), C1-C7alkoxide, —OTs, —OBn, halogen, C6-C10 aryls (optionally substituted with halo, hydroxyl, nitro, alkoxy, amido, nitrile, amine), C3-C6 cycloalkyl (optionally substituted with halo, hydroxyl, nitro, alkoxy, amido, nitrile, amine), C3-C6 cycloalkenes (optionally substituted with halo, hydroxyl, nitro, alkoxy, amido, nitrile, amine), heteroaryls (optionally substituted with halo, hydroxyl, nitro, alkoxy, amido, nitrile, amine), nitro, —OH, —NR6R7, —CN, —CONR8R9, —CO—R10; —COOR11;

R5 is selected from hydrogen, C1-C7 straight or branched alkyl (optionally substituted with halo, hydroxyl, nitro, alkoxy, amido, nitrile, amine), C2-C7 alkyl alkoxy where alkyl is C1-C3 and alkoxy is C1-C4, C6-C10 aryl (optionally substituted with halo, hydroxyl, nitro, alkoxy, amido, nitrile, amine), —COOR12, where R12 is C1-C4alkyl;

when R5 is —COOR12, R1 and R4 is hydrogen, R2 and R3 together may represent —O—CH2-O or a phenyl ring (optionally substituted with halo, hydroxyl, nitro, alkoxy, amido, nitrile, amine), R12 is C1-C4alkyl;

when, R5 is C1-C7 straight or branched alkyl (optionally substituted with halo, hydroxyl, nitro, alkoxy, amido, nitrile, amine), R1 is —OH, R4 is H, R2 and R3 together represent a heteroaryl (optionally substituted with halo, hydroxyl, nitro, alkoxy, amido, nitrile, amine).

In an embodiment of the present invention, wherein the compound of Formula II comprises;

a. (S)-Ethyl-2-((R)-1,3-dihydro-1-oxoisobenzofuran-3-yl)-2-hydroxyacetate (IIa
b. (S)-Ethyl-2-((R)-1,3-dihydro-5-methoxy-1-oxoisobenzofuran-3-yl)-2-hydroxy acetate (IIb);
c. (S)-Ethyl-2-((R)-1,3-dihydro-5,6-dimethoxy-1-oxoisobenzofuran-3-yl)-2-hydroxy acetate (IIc);
d. (S)-Ethyl-2-((R)-1,3-dihydro-6,7-dimethoxy-1-oxoisobenzofuran-3-yl)-2-hydroxy acetate (IId);
e. (S)-Ethyl-2-((R)-1,3-dihydro-5,7-dimethoxy-1-oxoisobenzofuran-3-yl)-2-hydroxy acetate (IIe);
f. (S)-Ethyl-2-((R)-1,3-dihydro-5,6,7-trimethoxy-1-oxoisobenzofuran-3-yl)-2-hydroxy acetate (IIf);
g. S)-Ethyl-2-((R)-5-(p-toluenesulfonoyloxy)-1,3-dihydro-6-methoxy-1-oxo iso benzo furan-3-yl)-2-hydroxyacetate (IIg);
h. (S)-Ethyl-2-((R)-5-(benzyloxy)-1,3-dihydro-6-methoxy-1-oxoisobenzofuran-3-yl)-2-hydroxyacetate (IIh);
i. (S)-Ethyl-2-((R)-5-fluoro-1,3-dihydro-1-oxoisobenzofuran-3-yl)-2-hydroxy acetate (IIi);
j. (S)-Ethyl-2-((R)-1,3-dihydro-5-nitro-1-oxoisobenzofuran-3-yl)-2-hydroxyacetate (IIj);
k. (S)-Ethyl 2-((R)-5-1,3-dihydro-5,6-dioxomethyl-1-oxoisobenzofuran-3-yl)-2-hydroxyacetate (IIk)
l. (S)-Ethyl 2-((R)-1,3-dihydro-1-oxonaphtho[2,1-c]furan-3-yl)-2-hydroxyl acetate (Il);
m. (R)-3-(Hydroxymethyl)isobenzofuran-1(3H)-one (IIm);
n. (R)-3-(Hydroxymethyl)-5-methoxyisobenzofuran-1(3H)-one (IIn);
o. (R)-3-(Hydroxymethyl)-5,6-dimethoxyisobenzofuran-1(3H)-one (IIo);
p. (R)-3-(Hydroxymethyl)-6,7-dimethoxyisobenzofuran-1(3H)-one (IIp);
q. (R)-3-(Hydroxymethyl)-5,7-dimethoxyisobenzofuran-1(3H)-one (IIq);
r. (R)-3-(Hydroxymethyl)-5,6,7-trimethoxyisobenzofuran-1(3H)-one (IIr);
s. (R)-1,3-Dihydro-1-(hydroxymethyl)-5-methoxy-3-oxoisobenzofuran-6-yl-4-methyl benzenesulfonate (IIs);
t. (R)-5-(Benzyloxy)-3-(hydroxymethyl)-6-methoxyisobenzofuran-1(3H)-one (IIt);
u. (R)-5-Fluoro-3-(hydroxymethyl)isobenzofuran-1(3H)-one (IIu);
v. (R)-3-(Hydroxymethyl)-5,6-dioxomethylisobenzofuran-1(3H)-one (IIv);
w. (R)-3-((R)-1-Hydroxy(butyl)isobenzofuran-1(3H)-one (IIw)
x. (R)-3-((R)-1-Hydroxy-2-tertiarybutyldimethylsilylethyl)-5,6 dimethoxyisobenzofuran-1(3H)-one (IIx)
y. (R)-3-((R)-Hydroxy(phenyl)methyl)-5,6-dimethoxyisobenzofuran-1(3H)-one (IIy)
z. (R)-3-((R)-1-Hydroxyheptyl)-5,6,7-trimethoxyisobenzofuran-1(3H)-one (IIz)

In one embodiment of the invention, wherein the solvent is selected from the group of polar protic solvents such as water, methanol, ethanol, n-propanol, isopropanol, n-butyl alcohol and t-butyl alcohol; polar aprotic solvents such as THF, DMF, DMSO, ethyl acetate; nonpolar organic solvent such as benzene, toluene, hexane, chloroform either alone or in combination thereof.

In another embodiment of the invention, wherein the solvent used is a mixture of t-BuOH, THF, water in the ratio of 0.5:0.5:1.

In yet another embodiment, wherein AD-mix-β contains potassium osmate $K_2OsO_2(OH)_4$ as the source of osmium tetroxide; potassium ferricyanide $K_3Fe(CN)_6$, which is the re-oxidant in the catalytic cycle; potassium carbonate; and chiral ligand selected from $(DHQD)_2PHAL$ which is phthalazine adduct with dihydroquinidine.

In still another embodiment, wherein yields and enantiomeric excess (ee) of chiral phthalides is in the range of 92-97% and 97-99% respectively.

In still another embodiment, a one pot asymmetric synthesis for preparation of compounds of general formula (III), wherein the said process comprising the steps of;

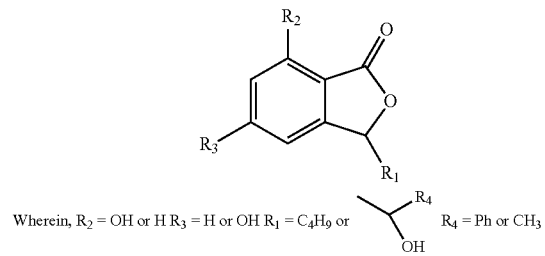

Wherein, $R_2$ = OH or H $R_3$ = H or OH $R_1$ = $C_4H_9$ or $R_4$ = Ph or $CH_3$
OH (a) preparing compounds of general formula (II) using process as claimed in claim 1;
(b) adding BBr3 and an organic solvent, preferably dichloromethane followed by stirring at temperature ranging between 10° C. to 25° C. for a period ranging 6-8 h to obtain compounds of general formula (III);
(c) optionally carrying out Barton-Mccombie deoxygenation of general formula (II) with 1,1-thiocarbonyl diimidazole in the presence of dichloromethane as solvent at room temperature ranging between 25-35° C. for 10-14 h followed by treatment with tributyltinhydride in the presence of catalytic amount of azobisisobutyronitrile for 20-40 min to obtain compounds of general formula (III).

In still another embodiment, wherein compounds of general formula (II) is used is selected from the group consisting of

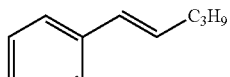

(E) 1-pent-1-enyl benzonitrile (Iw)

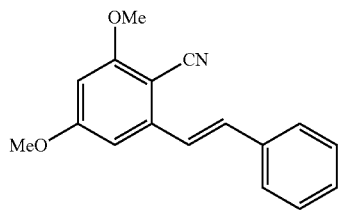

2,4-Dimethoxy-6-styrylbenzonitrile

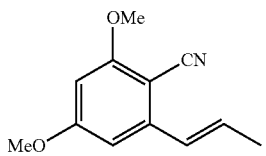

2,4-Dimethoxy-6-((E)-prop-1-enyl)-benzonitrile

In still another embodiment, wherein compounds of general formula (III) is used is selected from the group consisting of

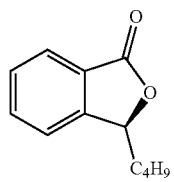

(S)-3-butylisobenzofuran-1(3H)-one

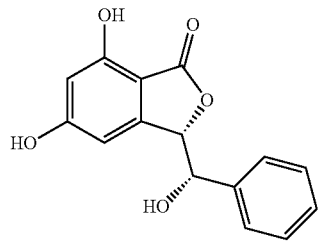

(S)-5,7-dihydroxy-3-((S)-hydroxy(phenyl)methyl)isobenzofuran-1-(3H)-one

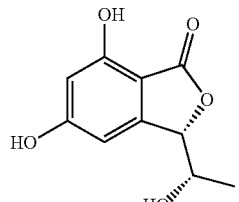

(S)-5,7-dihydroxy-3-((S)-1-hydroxyethyl)isobenzofuran-1(3H)-one

BRIEF DESCRIPTION OF FIGURES

FIG. 1 depicts Nosey spectra of IIa
FIG. 2 depicts HSQCGP spectra of Iia
FIG. 3 depicts HPLC chromatogram of IIa
FIG. 4 depicts HPLC chromatogram of IIb
FIG. 5 depicts HPLC chromatogram of IIc
FIG. 6 depicts HPLC chromatogram of Iid
FIG. 7 depicts HPLC chromatogram of IIe
FIG. 8 depicts HPLC chromatogram of IIn
FIG. 9 depicts HPLC chromatogram of IIo
FIG. 10 depicts HPLC chromatogram of IIp
FIG. 11 depicts HPLC chromatogram of IIq

DETAILED DESCRIPTION OF THE INVENTION

As used herein, "atom economic" refers and means to the conversion efficiency of the instant process in terms of all atoms involved (desired products produced) at ambient conditions, leading to less effluents.

The present invention relates to a single step, highly enantioselective catalytic oxidative cyclization process for the synthesis of 3-substituted chiral phthalides from o-cyano substituted aryl alkenes via synergetic acceleration due to CN and osmate ester groups in proximity positions, that leads to construction of phthalide framework in high yield and enantiomeric excess (ee), in short reaction time.

The present invention provides commercially feasible, atom economical, single step, highly enantioselective asymmetric dihydroxylation (AD) via nitrile accelerated oxidative cyclization of o-cyano substituted aryl alkenes for synthesis of 3-substituted chiral phthalides in high yield and purity in short reaction time.

In an embodiment, the present invention relates to single step, asymmetric dihydroxylation (AD) via synergetic acceleration due to CN and osmate ester groups in proximity positions of o-cyano substituted aryl alkenes of the general Formula I to obtain 3-substituted chiral phthalides of Formula II in high yield and enantiomeric excess.

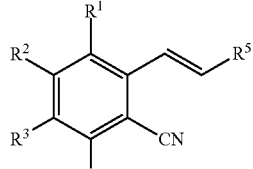

Formula I

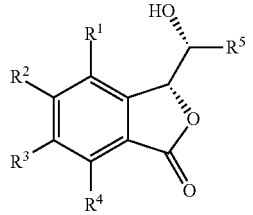

Formula II wherein, R1, R2, R3 and R4 are independently same or different groups selected from hydrogen, C1-C7 straight or branched alkyl (optionally substituted with halo, hydroxyl, nitro, alkoxy, amido, nitrile, amine), C2-C7 straight or branched alkenyl (optionally substituted with halo, hydroxyl, nitro, alkoxy, amido, nitrile, amine), C2-C7 straight or branched alkynyls (optionally substituted with halo, hydroxyl, nitro, alkoxy, amido, nitrile, amine), C1-C7alkoxide, —OTs, halogen, C6-C10 aryls (optionally substituted with halo, hydroxyl, nitro, alkoxy, amido, nitrile, amine), C3-C6 cycloalkyl (optionally substituted with halo, hydroxyl, nitro, alkoxy, amido, nitrile, amine), C3-C6 cycloalkenes (optionally substituted with halo, hydroxyl, nitro, alkoxy, amido, nitrile, amine), heteroaryls (optionally substituted with halo, hydroxyl, nitro, alkoxy, amido, nitrile, amine), nitro, —OH, —CN;

R5 is selected from hydrogen, C1-C7 straight or branched alkyl (optionally substituted with halo, hydroxyl, nitro, alkoxy, amido, nitrile, amine), C2-C7 alkyl alkoxy where alkyl is C1-C3 and alkoxy is C1-C4, C6-C10 aryl (optionally substituted with halo, hydroxyl, nitro, alkoxy, amido, nitrile, amine), —COOR12, where R12 is C1-C4alkyl;

when R5 is —COOR12, R1 and R4 is hydrogen, R2 and R3 together may represent —O—CH2-O or a phenyl ring (optionally substituted with halo, hydroxyl, nitro, alkoxy, amido, nitrile, amine), R12 is C1-C4alkyl;

when R5 is C1-C7 straight or branched alkyl (optionally substituted with halo, hydroxyl, nitro, alkoxy, amido, nitrile, amine), R1 is —OH, R4 is H, R2 and R3 together represent a heteroaryl (optionally substituted with halo, hydroxyl, nitro, alkoxy, amido, nitrile, amine).

The single step process for the synthesis of 3-substituted chiral phthalides of Formula II in high yield and purity, comprises, reacting o-cyano substituted aryl alkenes of the general Formula I with reagent AD-mix-β in presence of a polar solvent at ambient temperature for about 2-8 hours with intramolecular oxidative cyclization to obtain the desired product.

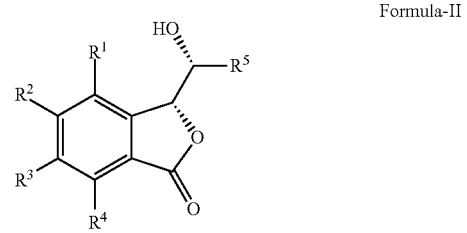

Formula-II wherein, R1, R2, R3 R4 and R5 are as described above.

The reagent AD-mix-β used in asymmetric dihydroxylation is a mixture of potassium osmate $K_2OsO_2(OH)_4$ as the source of osmium tetroxide; potassium ferricyanide $K_3Fe(CN)_6$, which is the re-oxidant in the catalytic cycle; potassium carbonate; and chiral ligand selected from $(DHQD)_2PHAL$ which is phthalazine adduct with dihydroquinidine.

The solvent for the process is selected from polar protic solvents such as water, methanol, ethanol, n-propanol, isopropanol, n-butyl alcohol and t-butyl alcohol; polar aprotic solvents such as THF, DMF, DMSO, ethyl acetate; nonpolar organic solvent such as benzene, toluene, hexane, chloroform either alone or in combination thereof in variable ratio; preferably a mixture of t-BuOH, THF, water in the ratio of 0.5:0.5:1 respectively. The temperature for the process is carried out at ambient temperature for about 2.0 to 8.5 hours.

Asymmetric dihydroxylation is performed in presence of osmium catalyst and a stoichiometric oxidant [e.g. $K_3Fe(CN)_6$ or N-methylmorpholine oxide (NMO)] in a buffered solution to ensure a pH range 8-10, since the reaction proceeds more rapidly under slightly basic conditions. Enantioselectivity is achieved through the addition of enantiomerically-enriched chiral ligands $(DHQD)_2PHAL$ which is phthalazine adduct with dihydroquinidine.

The intramolecular 5 exo-dig type oxidative cyclisation is assisted by the presence of a nitrile group which is in proximity to the alkene group in the compound of formula I.

The process is given below in Scheme-1.

Scheme 1:

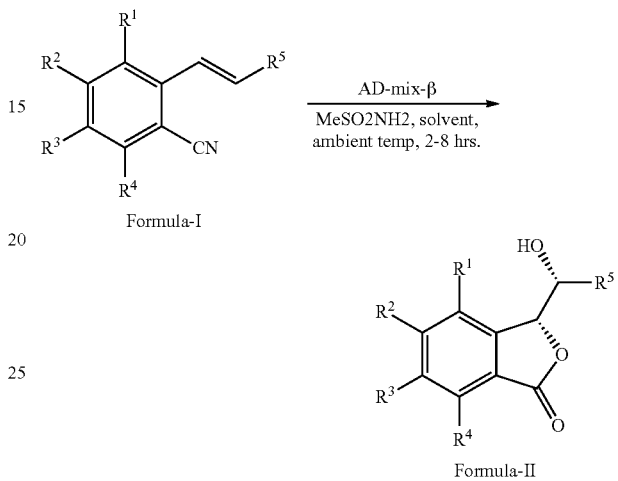

Formula-I

Formula-II wherein $R^1$-$R^5$ is as defined above;

The CN-assisted Os-catalysed oxidative cyclisation of compounds of Formula I (a'-j) to compounds of formula II (a'-j') is given below in Table 1,

TABLE 1

| Sr. No | $R^1$ | $R^2$ | $R^3$ | $R^4$ | $R^5$ | Yield (%)[a] | ee (%)[b] |
|---|---|---|---|---|---|---|---|
| a' | H | H | H | OMe | CO$_2$Et | 95 | 99 |
| b' | OMe | H | H | OMe | CO$_2$Et | 96 | 99 |
| c' | Cl | H | H | H | CO$_2$Et | 97 | 98 |
| d' | H | Cl | Cl | H | CO$_2$Et | 95 | 98[c] |
| e' | H | H | Cl | H | CO$_2$Et | 94 | 99 |
| f' | Ph | H | H | H | CO$_2$Et | 94 | 98[c] |
| g' | H | H | H | H | CH$_2$Ph | 95 | 98[c] |
| h' | H | H | H | H | CH$_2$OMe | 95 | 97[c] |

TABLE 1-continued

| | | | | | | | |
|---|---|---|---|---|---|---|---|
| i' | H | OMe | H | OMe | 4-OMeC$_6$H | 96 | 97[c] |
| j' | OMe | OMe | H | H | CO$_2$Et | 95 | 98 |

[a] Isolated yield after column chromatographic purification.
[b] ee determined by chiral HPLC analysis (see the ESI).
[c] cc determined by Mosher's ester analysis.

In one of the embodiment, the present invention relates to asymmetric dihydroxylation and nitrile assisted intramolecular 5 exo-dig type oxidative cyclisation of cyano-ethyl cinnamate, compound of Formula I (a-l);

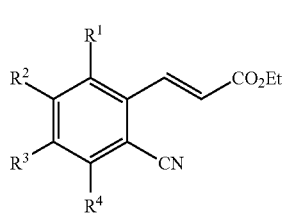

Formula-I (a-l)

The process is described below in Scheme 2; wherein the compounds of Formula I (a-l)) is subjected to single step asymmetric dihydroxylation and nitrile assisted intramolecular oxidative cyclisation using AD-mix β in presence of a mixture of t-BuOH, THF, water in the ratio of 0.5:0.5:1 respectively at room temperature for 6.5 to 8 hours to obtain chiral phthalides of Formula II (a-l)

Scheme 2:

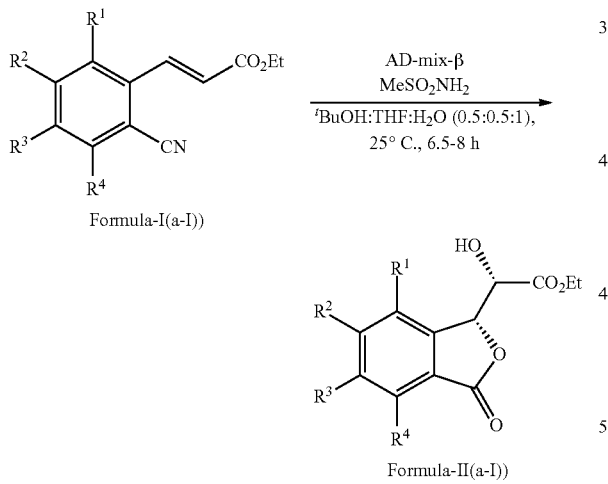

Formula-I(a-I))

Formula-II(a-I))

wherein; R1 is hydrogen and R2-R4 substituents are represented as in below Table 2:

| S. No | R$^2$ | R$^3$ | R$^4$ | Yield (%)[a] | ee (%)[b] |
|---|---|---|---|---|---|
| a | H | H | H | 94 | 99 |
| b | OMe | H | H | 95 | 99 |
| c | OMe | OMe | H | 94 | 99 |
| d | H | OMe | OMe | 94 | 99 |
| e | OMe | H | OMe | 94 | 99 |
| f | OMe | OMe | OMe | 92 | 99 |
| g | OTs | OMe | H | 93 | 99 |
| h | OBn | OMe | H | 94 | 99[c] |
| i | F | H | H | 94 | 99[c] |

-continued

| S. No | R$^2$ | R$^3$ | R$^4$ | Yield (%)[a] | ee (%)[b] |
|---|---|---|---|---|---|
| j | NO$_2$ | H | H | 93 | 99 |
| k | —O—CH$_2$—O— | | H | 95 | 98 |
| l | (E)-ethyl 3-(1-cyanonaphthalen-2-yl)acrylate | | | 94 | 98[c] |

[a] Isolated yield after column chromatographic purification.
[b] ee determined by chiral HPLC analysis (see the ESI).
[c] ee determined by Mosher's ester analysis.

In yet another embodiment, the process discloses asymmetric dihydroxylation and nitrile assisted intramolecular 5 exo-dig type oxidative cyclisation of cyano styrenics of Formula I (m-z).

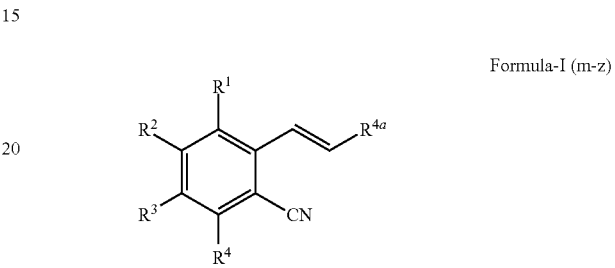

Formula-I (m-z)

The process is described below in Scheme 3; wherein the compound of Formula I (m-z) subjected to single step asymmetric dihydroxylation and nitrile assisted intramolecular oxidative cyclisation using AD-mix β in presence a mixture of t-BuOH, THF, water in the ratio of 0.5:0.5:1 respectively, at room temperature for 2.5 to 8 hours to obtain chiral phthalides of Formula II (m-z).

Scheme 3:

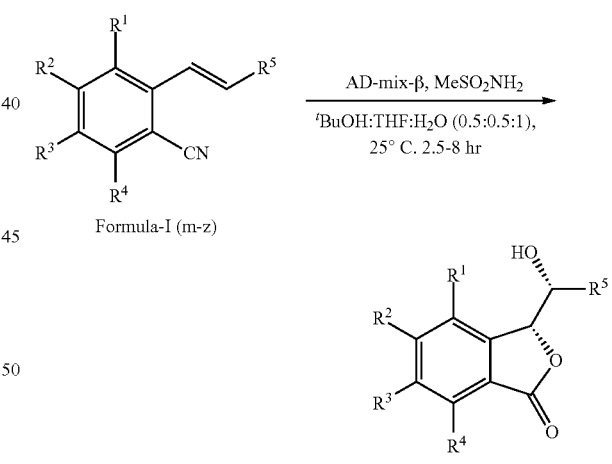

Formula-I (m-z)

Formula-II (m-z)

wherein; R1 is hydrogen, and R2-R5 substituents are represented as in below Table 3:

| S. No | R$^2$ | R$^3$ | R$^4$ | R$^5$ | Yield (%)[a] | ee (%)[b] |
|---|---|---|---|---|---|---|
| m | H | H | H | H | 95 | 99 |
| n | OMe | H | H | H | 95 | 98 |
| o | OMe | OMe | H | H | 93 | 98 |
| p | H | OMe | OMe | H | 94 | 99 |
| q | OMe | H | OMe | H | 94 | 99 |

-continued

| S. No | R² | R³ | R⁴ | R⁵ | Yield (%)[a] | ee (%)[b] |
|---|---|---|---|---|---|---|
| r | OMe | OMe | OMe | H | 93 | 98 |
| s | OTs | OMe | H | H | 95 | 98[c] |
| t | OBn | OMe | H | H | 94 | 99 |
| u | F | H | H | H | 93 | 98[c] |
| v | —O—CH₂—O— | | H | H | 94 | 98[c] |
| w | H | H | H | C₃H₇ | 93 | 97 |
| x[d] | OMe | OMe | H | CH₂OTBS | 94 | 97[c] |
| y[d] | OMe | OMe | H | Ph | 94 | 97[c] |
| z[d] | OMe | OMe | H | n-C₆H₁₃ | 92 | 98[c] |

[a]Isolated yield after column chromatographic purification.
[b]ee determined by chiral HPLC analysis (see the ESI).
[c]ee determined by Mosher's ester analysis.
[d]MeSO₂NH₂ (1 equiv.) was used in the reaction.

In yet another embodiment, the present invention provides "one-pot" asymmetric synthesis of biologically important natural compounds having 3-substituted chiral phthalide structural framework in the molecule. The process for the synthesis of bioactive natural compounds (1, 2 and 3) and their intermediates is given below in Scheme 4 and 5.

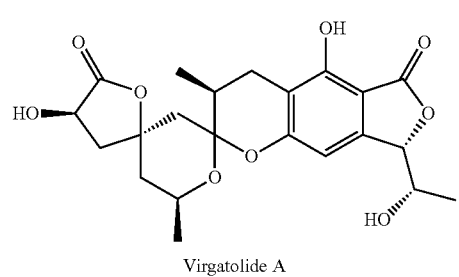

Virgatolide A (1)

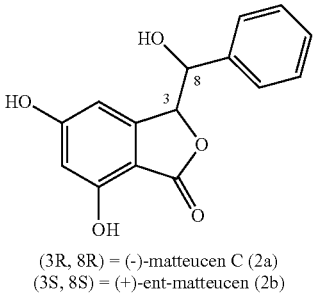

(3R, 8R) = (−)-matteucen C (2a)
(3S, 8S) = (+)-ent-matteucen (2b)
(3R, 8S) = (−)-matteucen D (2c)
(3S, 8R) = (+)-ent-matteuen D (2d)

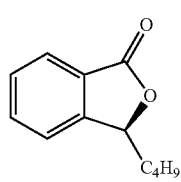

Butylphthalide (3)

The process for the preparation of biological compound 3-butylphthalide (3) is given below in Scheme 4.

Scheme 4: Concise synthesis of 3-butylphthalide (3)

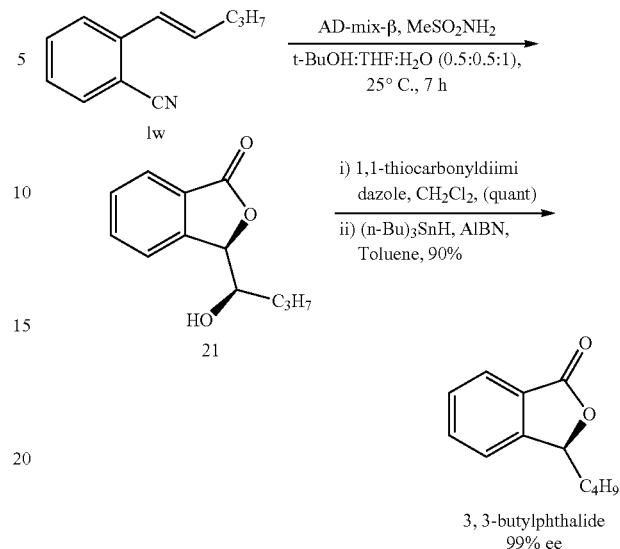

In the synthesis, compound 16 is subjected to asymmetric dihydroxylation (AD) and nitrile accelerated oxidative cyclization to obtain intermediate chiral phthalide 21 followed by deoxygenation using Barton-McCombie reaction to obtain bioactive compound 3.

Synthesis of demethyl pestaphthalide of Formula 20, an intermediate in the biosynthesis of virgatolide-A (FIG. 1, compound 1) and Mattucen C compound of formula 2a are given below in
Scheme 5.

Scheme 5: Short synthesis of demethyl pestaphthalide (20) and matteucen C (2a)

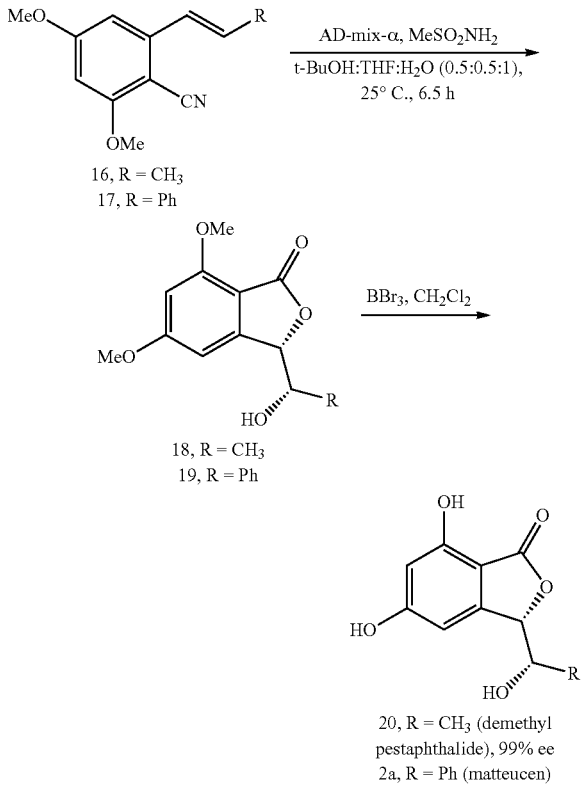

The synthesis of bioactive natural compounds and their intermediates of Formula 3, 20 and 2a-d is carried out in two steps comprising;
(i) asymmetric dihydroxylation (AD) and nitrile accelerated oxidative cyclization of o-cyano substituted aryl alkenes of Formula 16 and 17 to obtain intermediate chiral phthalide compounds of Formula 18 and 19 respectively;
(ii) deoxygenation of compound of formula 21 using Barton-McCombie reaction to obtain compound of formula 3 or demethylation with $BBr_3$ of compounds 18 and 19 to obtain compounds 20 and 2a respectively.

It is observed that the asymmetric synthesis of all four stereoisomers of Matteucen C and D (2a-d) establishes the stereochemical syn and anti relationship of C-3 and C-8 positions.

The bioactive compound, Virgatolide-A (1) exhibits cytotoxic activity against HeLa cells. Compound Mattucen (2a-d) is used for the treatment of hemostatics and in relieving ostalgia while compound 3-butylphthalide is used as anti-convulsant drug for the treatment of stroke.

In view of above, present invention provides a novel CN-assisted Os-catalyzed oxidative cyclization via AD process of o-cyano substituted aryl alkenes for the synthesis of wide variety of 3-substituted chiral phthalides and their structural analogues. The so obtained chiral phthalides have excellent enantioselectivities of 97-99% and high product yield in the range of 92-97%.

The synergism shown by CN and osmate ester in proximity enhance the rate of the reaction to obtain intramolecular oxidative cyclized compound as a chiral phthalide, the instant synthetic route enables the "one-pot" synthesis of biologically important natural products such as virgatolide A, matteucen C and D, butylphthalide with high optical purities, also useful for total synthesis of other bioactive phthalides frameworks.

The present inventors, have concluded that the combination of CN and alkene bond in proximity position enhances the rate of the asymmetric catalytic oxidative cyclization of a wide range of o-cyano substituted aryl alkene substrates leading to highly enantioselective synthesis of 3-substituted chiral phthalides in short reaction time as disclosed and claimed in the present invention.

The process of the instant invention, thus, features broad substrate scope and good functional group tolerance. Further, the process is easy to perform at ambient conditions, making it energy saving and economic. The process is also eco-friendly, as a single step atom economic reaction generates relatively less effluents. Moreover, the short reaction time also contributes to saving of energy and process cost including labour and equipment use.

EXAMPLES

The following examples are given by way of illustration and therefore should not be construed to limit the scope of the present invention.

(A) Experimental Study:

To account for the mechanistic aspect of the present invention and to establish the stereochemistry of the cyclized product, the following experiments were conducted as shown in Scheme 6 below:

Scheme 6

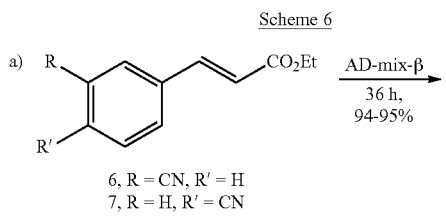

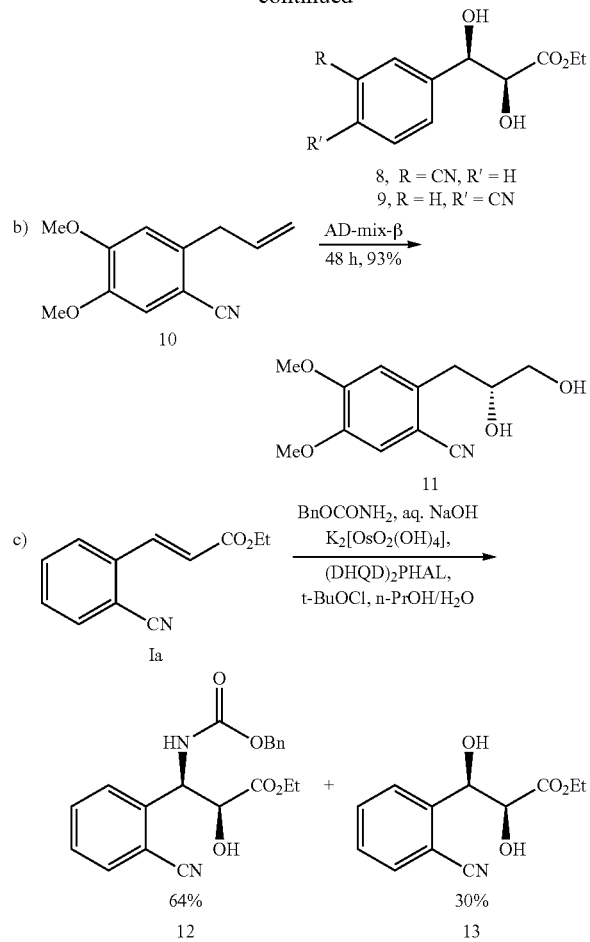

It was observed that (i) AD-mix-β of substrates 6, 7 or 10 for 48 hr gave the corresponding cyanodiols 8, 9 or 11 respectively, indicating that both CN and C=C groups must be positioned in proximity for CN coordination assistance to take place; (ii) asymmetric aminohydroxylation of Ia, in addition gave the expected amino alcohol 12 (64%) along with diol 13 (30%) (Scheme 6), with no phthalide formation, suggesting that coordination of CN onto imino osmate ester was thermodynamically less favorable, due to its reduced Lewis acid character. Hence, the inventors of present invention inferred that mere asymmetric dihydroxylation or amino hydroxylation process were not enabled to yield chiral phthalide with high yield and optical purity. The inventors of present invention directed asymmetric dihydroxylation with specific reaction condition, wherein o-cyano substituted aryl alkene of Formula Ia and Iw were subjected to asymmetric dihydroxylation using AD-mix-β in presence of a mixture of t-BuOH, THF, water in the ratio of 0.5:0.5:1 respectively at room temperature which resulted in an intermediate A as shown below in Scheme 7 in which co-ordination of CN to Os(VI) and concurrent attack of osmate ester onto electropositive carbon of CN helped to accelerate the hydrolysis of osmate ester resulting in 5-exo-dig type cyclization to afford iminoester 15a-b in 20% which lead to formation of chiral phthalides. The study clearly excludes the possibility of hydrolysis of CN to $CO_2H$ followed by cyclization, whereas addition of benzonitrile as external source of CN-assistance resulted in no rate enhancement for the AD process.

The mechanism for nitrile-assisted osmium-catalyzed oxidative cyclization is disclosed in scheme 7 as follows;

Scheme 7:

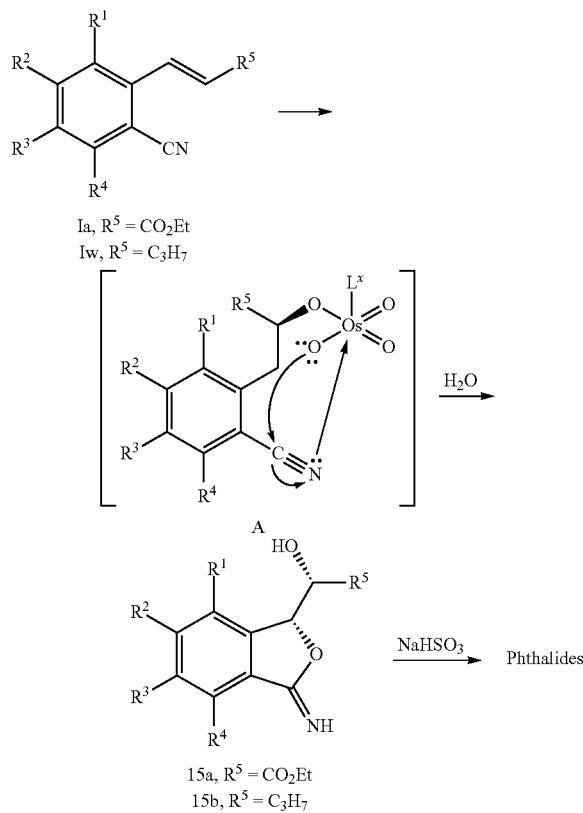

wherein $R^1$-$R^4$ substituents are as defined above.

(B) A General Experimental Procedure for the Preparation of Cyano Cinnamates and Styrenics (Ia-v):

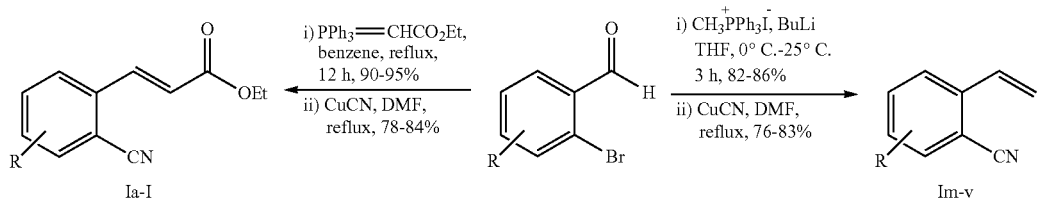

Scheme 8: Synthesis of o-Cyano Olefins I a-l & I m-v

General Experimental Procedure for the Preparation of Cyano Cinnamates (I a-l)

To a stirred solution of substituted 2-bromobenzaldehydes (50 mmol) in benzene (100 mL), Ph3P=CHCO2Et (55 mmol) was added. It was refluxed for 4 h under N2 atmosphere. After the completion of reaction, benzene was distilled out to give the crude product, which was purified by column chromatography [silica gel (230-400 mesh) and petroleum ether:Ethyl acetate (90:10) as eluent] to afford pure product 2-bromo-ethyl cinnamates in 94% yield. The product was taken in dry DMF (20 mL) and CuCN (15.6 mmol) was added and refluxed under N2 for 18 h (monitored by TLC). The reaction mixture was cooled to room temperature, diluted with water (30 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (70:30) as an eluent] gave 2-cyano-ethyl cinnamate in 82% yield.

Example 1

(E)-Ethyl 3-(2-cyanophenyl)acrylate (Ia): (Substituted 2-bromobenzaldehydes: 2-Bromo benzaldehyde)

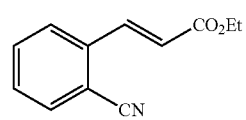

Yield: 88% (for two steps), colorless solid; mp 60-62° C.; IR (CHCl3): 765, 784, 1031, 1184, 1318, 1447, 1480, 1594, 1640, 1712, 2225, 2938, 2983 cm-1; 1H NMR (200 MHz, CDCl3): δ 1.36 (t, J=7.3 Hz, 3H), 4.31 (q, J=7.3 Hz, 2H), 6.60 (d, J=16 Hz, 1H), 7.47 (td, J=1.44, 7.55 Hz, 1H), 7.62 (td, J=1.44, 7.55 Hz, 1H), 7.70-7.76 (m, 2H), 7.96 (d, J=16 Hz, 1H); 13C NMR (CDCl3): δ 14.1, 60.7, 112.5, 116.8, 122.9, 126.8, 129.9, 132.8, 133.3, 137.1, 139.1, 165.4; Analysis: C12H11NO2 requires C, 71.63; H, 5.51; N, 6.96. found C, 71.59; H, 5.56; N, 6.93%.

Example 2

(E)-Ethyl 3-(2-cyano-5-methoxyphenyl)acrylate (Ib): (Substituted 2-bromobenzaldehydes: 5-methoxy, 2-bromo benzaldehyde)

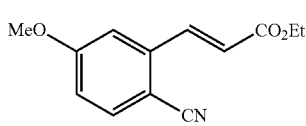

Yield: 86% (for two steps), colorless solid; mp 130-132° C.; IR (CHCl3): 728, 868, 1026, 1256, 1490, 1594, 1607, 1640, 1712, 2228, 2853, 2923 3023 cm-1; 1H NMR (200 MHz, CDCl3): δ 1.36 (t, J=7.08 Hz, 3H), 3.90 (s, 3H), 4.29

(q, J=7.08 Hz, 2H), 6.56 (d, J=16 Hz, 1H), 6.97 (dd, J=2.54, 8.73 Hz, 1H), 7.15 (d, J=2.54 Hz, 1H), 7.63 (d, J=8.79 Hz, 1H), 7.90 (d, J=16 Hz, 1H); 13C NMR (CDCl3): δ 14.2, 55.6, 60.8, 104.6, 112.1, 116.0, 117.3, 123.1, 135.0, 139.4, 162.7, 165.5; Analysis: C13H13NO3 requires C, 67.52; H, 5.67; N, 6.06 found C, 67.49; H, 5.61; N, 6.01%.

Example 3

(E)-Ethyl 3-(2-cyano-4,5-dimethoxyphenyl)acrylate (1c): (Substituted 2-bromobenzaldehydes: 4,5-dimethoxy, 2-bromo benzaldehyde)

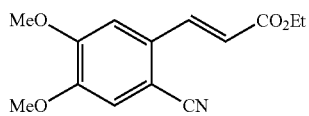

Yield: 87% (for two steps), colorless solid; mp 159-161° C.; IR (CHCl3): 761, 848, 1094, 1149, 1204, 1326, 1462, 1571, 1594, 1709, 2222, 2984, 3018 cm-1; 1H NMR (200 MHz, CDCl3): δ 1.36 (t, J=7.36 Hz, 3H), 3.94 (s, 3H), 3.97 (s, 3H), 4.29 (q, J=7.36 Hz, 2H), 6.47 (d, J=16.03 Hz, 1H), 7.07 (s, 1H), 7.11 (s, 1H), 7.89 (d, J=16.03 Hz, 1H); 13C NMR (CDCl3): δ 14.2, 55.9, 56.2, 60.7, 105.2, 108.2, 114.2, 117.1, 120.7, 131.5, 139.2, 150.5, 152.6, 165.8; Analysis: C14H15NO4 requires C, 64.36; H, 5.79; N, 5.36. found C, 64.32; H, 5.71; N, 5.34%.

Example 4

(E)-Ethyl 3-(2-cyano-3,4-dimethoxyphenyl)acrylate (Id): (Substituted 2-bromobenzaldehydes: 3,4-dimethoxy, 2-bromo benzaldehyde)

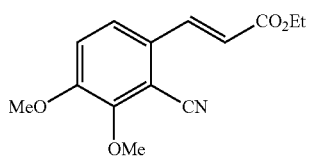

Yield: 88% (for two steps), colorless solid; mp 145-147° C.; IR (CHCl3): 758, 894, 1078, 1138, 1208, 1318, 1326, 1462, 1571, 1594, 1608, 1710, 2222, 2984, 3018 cm-1; 1H NMR (200 MHz, CDCl3): δ 1.35 (t, J=7.05 Hz, 3H), 3.93 (s, 3H), 4.03 (s, 3H), 4.27 (q, J=7.05 Hz, 2H), 6.48 (d, J=16 Hz, 1H), 7.10 (d, J=8.65 Hz, 1H), 7.40 (d, J=8.65 Hz, 1H), 7.83 (d, J=16 Hz, 1H); 13C NMR (CDCl3): δ 14.3, 56.1, 60.6, 61.6, 107.9, 114.1, 116.4, 120.7, 122.9, 129.7, 139.2, 152.1, 153.5, 165.9; Analysis: C14H15NO4 requires C, 64.36; H, 5.79; N, 5.36. found C, 64.34; H, 5.71; N, 5.32%.

Example 5

(E)-Ethyl 3-(2-cyano-3,5-dimethoxyphenyl)acrylate (Ie) (substituted 2-bromobenzaldehydes: 3,5-dimethoxy, 2-bromo benzaldehyde)

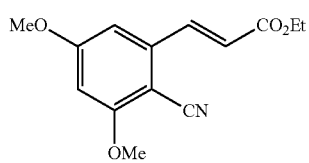

Yield: 87% (for two steps), colorless solid; mp 119-122° C.; IR (CHCl3): 734, 876, 1069, 1128, 1208, 1326, 1326, 1478, 1568, 1594, 1608, 1712, 2228, 2958, 3082 cm-1; 1H NMR (200 MHz, CDCl3): δ 1.36 (t, J=7.15 Hz, 3H), 3.89 (s, 3H), 3.93 (s, 3H), 4.29 (q, J=7.15 Hz, 2H), 6.47 (d, J=2.13 Hz, 1H), 6.55 (d, J=16 Hz, 1H), 6.73 (d, J=2.13 Hz, 1H), 7.86 (d, J=16 Hz, 1H); 13C NMR (CDCl3): δ 14.3, 55.7, 56.1, 60.8, 94.9, 96.1 99.4, 103.4, 114.8, 123.3, 139.6, 140.1, 163.4, 163.9, 165.6; Analysis: C14H15NO4 requires C, 64.36; H, 5.79; N, 5.36 found C, 64.32; H, 5.71; N, 5.34%.

Example 6

(E)-Ethyl 3-(2-cyano-3,4,5-trimethoxyphenyl)acrylate (If) (substituted 2-bromobenzaldehydes: 3,4,5-trimethoxy, 2-bromo benzaldehyde)

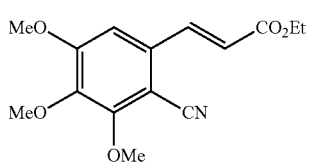

Yield: 88% (for two steps), colorless solid; mp 150-152° C.; IR (CHCl3): 669, 703, 749, 940, 1260, 1311, 1573, 1607, 1640, 1708, 2210, 2979, 3016 cm-1; 1H NMR (200 MHz, CDCl3): δ 1.36 (t, J=7.15 Hz, 3H), 3.90 (s, 3H), 3.96 (s, 3H), 4.06 (s, 3H), 4.28 (q, J=7.15 Hz, 2H), 6.50 (d, J=16 Hz, 1H), 6.91 (s, 1H), 7.84 (d, J=16 Hz, 1H); 13C NMR (CDCl3): δ 14.3, 55.8, 60.3, 109.1, 115.4, 117.0, 118.5, 126.2, 142.5, 148.5, 151.1, 161.2; Analysis: C15H17NO5 requires C, 61.85; H, 5.88; N, 4.81 found C, 61.82; H, 5.79, N, 4.75%.

Example 7

5-((E)-2-(Ethoxycarbonyl)vinyl)-4-cyano-2-methoxyphenyl 4-methylbenzenesulfonate (Ig): (substituted 2-bromobenzaldehydes: 5 tosyl 4 methoxy 2-bromo benzaldehyde)

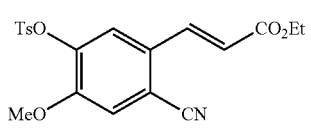

Yield: 87% (for two steps), colorless solid; mp 150-151° C.; IR (CHCl3): 742, 865, 1030, 1128, 1232, 1318, 1329, 1478, 1571, 1594, 1608, 1708, 2225, 2982, 3025 cm-1; 1H NMR (200 MHz, CDCl3): δ 1.35 (t, J=6.90 Hz, 3H), 2.48 (s, 3H), 3.73 (s, 3H), 4.30 (q, J=6.90 Hz, 2H), 6.54 (d, J=16 Hz, 1H), 7.09 (s, 1H), 7.35 (d, J=8.5 Hz, 2H), 7.39 (s, 1H), 7.77 (d, J=8.5 Hz, 2H), 7.91 (d, J=16 Hz, 1H); 13C NMR (CDCl3): δ 14.2, 21.7, 56.0, 61.0, 104.5, 110.3, 116.0, 123.8, 128.3, 129.7, 132.6, 137.9, 138.4, 139.1, 145.8, 155.6, 165.2; Analysis: C20H19NO6S requires C, 59.84; H, 4.77; N, 3.49. found C, 59.78; H, 4.69; N, 3.42%.

Example 8

(E)-Ethyl 3-(5-(benzyloxy)-2-cyano-4-methoxyphenyl)acrylate (Ih): (Substituted 2-bromobenzaldehydes: 5 benzyloxy 4 methoxy 2-bromo benzaldehyde)

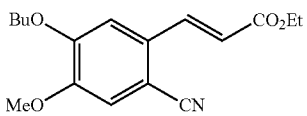

Ih

Yield: 86% (for two steps), colorless solid; mp 146-148° C.; IR (CHCl3): 738, 825, 1031, 1098, 1234, 1334, 1380, 1467, 1568, 1575, 1608, 1710, 2228, 2982, 3034 cm-1; 1H NMR (200 MHz, CDCl3): δ 1.35 (t, J=7.23 Hz, 3H), 3.93 (s, 3H), 4.28 (q, J=7.33 Hz, 2H), 5.20 (s, 2H), 6.34 (d, J=15.48 Hz, 1H), 7.08 (s, 2H), 7.34-7.43 (m, 5H), 7.84 (d, J=15.48 Hz, 1H); 13C NMR (CDCl3): δ 14.3, 56.2, 60.8, 71.0, 105.5, 110.5, 114.7, 117.2, 120.9, 127.3, 128.8, 131.5, 135.4, 139.3, 151.1, 151.8, 165.9; Analysis: C20H19NO4 requires C, 71.20; H, 5.68; N, 4.15. found C, 71.14; H, 5.61; N, 4.09%.

Example 9

(E)-Ethyl 3-(5-cyanobenzo[d][1,3]dioxol-6-yl)acrylate (Ik): (Substituted 2-bromobenzaldehydes: 2-bromo pipernal)

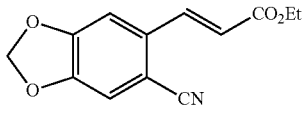

Ik

Yield: 86% (for two steps), white solid; mp 148-149° C.; IR (CHCl3): 728, 878, 1042, 1134, 1256, 1366, 1382, 1478, 1568, 1594, 1608, 1712, 2218, 2958, 3082 cm-1; 1H NMR (200 MHz, CDCl3): δ 1.35 (t, J=7.06 Hz, 3H), 4.28 (q, J=7.06 Hz, 2H), 6.12 (s, 2H), 6.41 (d, J=15.88 Hz, 1H), 7.05 (s, 1H), 7.13 (s, 1H), 7.90 (d, J=15.88 Hz, 1H); 13C NMR (CDCl3): δ 14.3, 60.8, 102.8, 105.9, 106.8, 111.8, 116.9, 121.4, 133.9, 138.9, 149.2, 151.9, 165.7; Analysis: C13H11NO4 requires C, 63.67; H, 4.52; N, 5.71. found C, 63.59; H, 4.48; N, 5.65%.

Example 10

(E)-Ethyl 3-(1-cyanonaphthalen-2-yl)acrylate (Il): (Substituted 2-bromobenzaldehydes: 1-bromo naphathaldehyde)

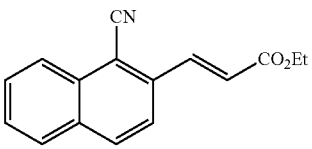

Il

Yield: 88% (for two steps), colorless solid; mp 118-119° C.; IR (CHCl3): 784, 865, 989, 1030, 1106, 1210, 1275, 1291, 1319, 1368, 1573, 1607, 1712, 2218, 2978, 3084 cm-1; 1H NMR (200 MHz, CDCl3): δ 1.35 (t, J=7.03 Hz, 3H), 4.32 (q, J=7.03 Hz, 2H), 6.68 (d, J=16 Hz, 1H), 7.59-7.78 (m, 3H), 7.90 (d, J=7.70 Hz, 1H), 8.04 (d, J=8.78 Hz, 1H), 8.19 (d, J=16 Hz, 1H), 8.28 (d, J=8.78 Hz, 1H); 13C NMR (CDCl3): δ 14.2, 60.8, 110.8, 115.5, 122.1, 123.5, 125.8, 128.3, 129.1, 132.5, 132.9, 137.0, 139.5, 165.5; Analysis: C16H13NO2 requires C, 76.48; H, 5.21; N, 5.57. found C, 76.42; H, 5.19; N, 5.52%.

General Experimental Procedure for the Preparation of Cyano Styrenes (Im-v)

To a stirred solution of methyltriphenylphosphonium iodide (1.05 eq) in THF was added n-butyl lithium in hexane (1.05 eq), the solution was stirred for 30 min at 0° C. and substituted 2-bromo benzaldehydes (1.0 eq) in THF was added drop wise via syringe at the same temperature and the reaction mixture was allowed to stir for 90 min at room temperature (monitored by TLC). The reaction mixture was cooled to 0° C., followed by dilution with sat. NH4Cl (25 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (90:10) as an eluent] gave 2-bromostyrenes in 86% yield. The product was taken in dry DMF (20 mL) and CuCN (15.6 mmol) was added and refluxed under N2 for 18 h (monitored by TLC). The reaction mixture was cooled to room temperature, diluted with water (30 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (70:30) as an eluent] gave 2-cyano-ethyl cinnamates in 86% yield.

Example 11

2-Vinylbenzonitrile (Im): (Substituted 2-bromobenzaldehydes: 2-bromo benzaldehyde)

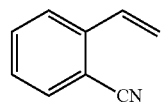

Im

Yield: 86% (for two steps), Gum; IR (CHCl3): 752, 839, 962, 1014, 1072, 1118, 1202, 1308, 1347, 1368, 1444, 1573, 1607, 1625, 1675, 2215, 2889, 2923, 3012 cm-1; 1H NMR (200 MHz, CDCl3): 5.54 (d, J=10.64 Hz, 1H), 5.95 (d, J=17.83 Hz, 1H), 7.08 (dd, J=10.64, 17.83 Hz, 1H), 7.34 (td, J=1.28, 7.59 Hz, 1H), 7.51-7.70 (m, 3H); 13C NMR (CDCl3): δ 111.0, 117.4, 118.7, 125.2, 127.8, 132.5, 132.7, 140.4; Analysis: C9H7N requires C, 83.69; H, 5.46; N, 10.84. found C, 83.62; H, 5.41; N, 10.78%.

Example 12

4-Methoxy-2-vinylbenzonitrile (In): (Substituted 2-bromobenzaldehydes: 5-methoxy, 2-bromo benzaldehyde)

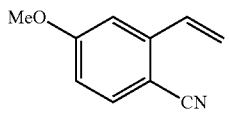

Yield: 84% (for two steps), Gum, IR (CHCl3): 752, 839, 1030, 1083, 1119, 1256, 1308, 1347, 1368, 1456, 1573, 1607, 1625, 1668, 2208, 2923, 3081 cm-1; 1H NMR (200 MHz, CDCl3): 3.88 (s, 3H), 5.53 (d, J=11.10 Hz, 1H), 5.92 (d, J=17.76 Hz, 1H), 6.85 (dd, J=2.30, 8.54 Hz, 1H), 7.03 (dd, J=11.10, 17.76 Hz, 1H), 7.11 (s, 1H), 7.55 (d, J=8.54 Hz, 1H); 13C NMR (CDCl3): δ 55.4, 103.2, 110.4, 114.1, 117.9, 118.7, 132.9, 134.4, 142.5, 162.7; Analysis: C10H9NO requires C, 75.45; H, 5.70; N, 8.80. found C, 75.41; H, 5.67; N, 8.73%.

Example 13

4,5-Dimethoxy-2-vinylbenzonitrile (Io): (Substituted 2-bromobenzaldehydes: 4,5-dimethoxy, 2-bromo benzaldehyde)

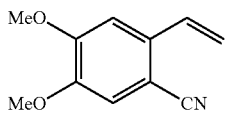

Yield: 88% (for two steps), colorless solid; mp 106-107° C.; IR (CHCl3): 752, 839, 936, 1031, 1086, 1119, 1256, 1308, 1378, 1389, 1456, 1575, 1612, 1628, 1656, 2210, 2923, 3052 cm-1; 1H NMR (200 MHz, CDCl3): 3.91 (s, 3H), 3.97 (s, 3H), 5.45 (d, J=11.08 Hz, 1H), 5.80 (d, J=17.28 Hz, 1H), 6.94-7.08 (m, 3H); 13C NMR (CDCl3): δ 55.7, 55.9, 102.7, 106.9, 113.5, 116.5, 117.7, 132.5, 134.9, 148.7, 152.5; Analysis: C11H11NO2 requires C, 69.83; H, 5.86; N, 7.40. found C, 69.75; H, 5.75; N, 7.39%.

Example 14

2,3-Dimethoxy-6-vinylbenzonitrile (Ip): (Substituted 2-bromobenzaldehydes: 3,4-dimethoxy, 2-bromo benzaldehyde)

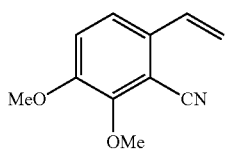

Yield: 86% (for two steps), colorless solid; mp 108-110° C.; IR (CHCl3): 748, 840, 936, 1028, 1086, 1119, 1256, 1308, 1378, 1389, 1456, 1575, 1612, 1628, 1656, 2202, 2981, 3029 cm-1; 1H NMR (200 MHz, CDCl3): 3.88 (s, 3H), 3.90 (s, 3H), 5.53 (d, J=10.99 Hz, 1H), 5.90 (d, J=17.31 Hz, 1H), 6.37 (d, J=2.20 Hz, 1H), 6.69 (d, J=2.20 Hz, 1H), 7.01 (dd, J=10.99, 17.31 Hz, 1H); 13C NMR (CDCl3): δ 56.1, 61.5, 106.7, 114.7, 116.7, 120.8, 132.4, 133.4, 151.5, 151.7; Analysis: C11H11NO2 requires C, 69.83; H, 5.86; N, 7.40. found C, 69.73; H, 5.78; N, 7.39%.

Example 15

2,4-Dimethoxy-6-vinylbenzonitrile (Iq): (Substituted 2-bromobenzaldehydes: 3,5-dimethoxy, 2-bromo benzaldehyde)

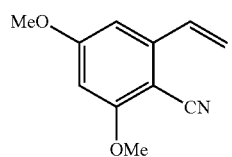

Yield: 83% (for two steps), colorless solid; mp 76-79° C.; IR (CHCl3): 724, 867, 968, 1030, 1086, 1119, 1259, 1308, 1386, 1389, 1456, 1578, 1612, 1636, 1656, 2212, 2985, 3029 cm-1; 1H NMR (200 MHz, CDCl3): 3.90 (s, 3H), 4.00 (s, 3H), 5.40 (d, J=10.83 Hz, 1H), 5.79 (d, J=17.68 Hz, 1H), 6.94 (dd, J=10.83, 17.68 Hz, 1H), 7.07 (d, J=8.55 Hz, 1H), 7.32 (d, J=8.55 Hz, 1H); 13C NMR (CDCl3): δ 55.5, 55.9, 93.6, 97.5, 101.7, 115.5, 118.9, 133.1, 143.4, 163.0, 163.8; Analysis: C11H11NO2 requires C, 69.83; H, 5.86; N, 7.40. found C, 69.79; H, 5.78; N, 7.39%.

Example 16

2,3,4-Trimethoxy-6-vinylbenzonitrile (Ir): (Substituted 2-bromobenzaldehydes: 3,4,5-trimethoxy, 2-bromo benzaldehyde)

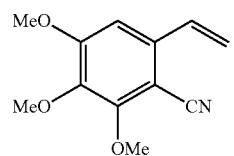

Yield: 87% (for two steps), white solid; mp 102-103° C.; IR (CHCl3): 771, 867, 1051, 1105, 1204, 1238, 1257, 1580, 1609, 1753, 2228, 2979, 3013 cm-1; 1H NMR (200 MHz, CDCl3): 3.86 (s, 3H), 3.95 (s, 3H), 4.04 (s, 3H), 5.48 (d, J=11.28 Hz, 1H), 5.83 (d, J=17.32 Hz, 1H), 6.85 (s, 1H), 6.97 (dd, J=11.28, 17.32 Hz, 1H); 13C NMR (CDCl3): δ 55.9, 60.8, 61.5, 98.7, 103.4, 114.8, 117.8, 132.6, 137.2, 141.1, 155.4, 157.2; Analysis: C12H13NO3 requires C, 65.74; H, 5.98; N, 6.39. found C, 65.72; H, 5.91; N, 6.37%.

Example 17

4-Cyano-2-methoxy-5-vinylphenyl 4-methylbenzenesulfonate (Is): (Substituted 2-bromobenzaldehydes: 5 tosyl 4 methoxy 2-bromo benzaldehyde)

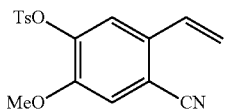

Yield: 82% (for two steps), colorless solid; mp 149-150° C.; IR (CHCl3): 746, 845, 938, 1034, 1086, 1119, 1256, 1308, 1378, 1389, 1456, 1575, 1612, 1628, 1656, 2220, 2978, 3075 cm-1; 1H NMR (200 MHz, CDCl3): 2.48 (s, 3H), 3.74 (s, 3H), 5.57 (d, J=10.95 Hz, 1H), 5.86 (d, J=17.62 Hz, 1H), 6.93-7.08 (m, 2H), 7.28 (s, 1H), 7.35 (d, J=8.01 Hz, 2H), 7.77 (d, J=8.24 Hz, 2H); 13C NMR (CDCl3): δ 21.7, 55.8, 102.9, 108.9, 116.6, 119.7, 127.7, 128.5, 129.6, 132.3, 132.7, 137.7, 141.4, 145.6, 155.5; Analysis: C17H15NO4S requires C, 61.99; H, 4.59; N, 4.25. found C, 61.89; H, 4.53; N, 4.23%.

Example 18

4-(Benzyloxy)-5-methoxy-2-vinylbenzonitrile (It): (Substituted 2-bromobenzaldehydes: 5 benzyloxy 4 methoxy 2-bromo benzaldehyde)

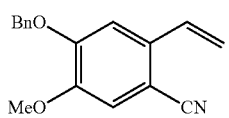

Yield: 84% (for two steps), colorless solid; mp 111-113° C.; IR (CHCl3): 747, 858, 934, 1028, 1065, 1119, 1232, 1308, 1394, 1389, 1456, 1574, 1612, 1631, 1656, 2220, 2988, 3086 cm-1; 1H NMR (200 MHz, CDCl3): 3.90 (s, 3H), 5.21 (s, 2H), 5.39 (d, J=11.15 Hz, 1H), 5.66 (d, J=17.45 Hz, 1H), 6.89-7.04 (m, 2H), 7.10 (s, 1H), 7.32-7.47 (m, 5H); 13C NMR (CDCl3): δ 56.0, 70.8, 103.1, 109.2, 114.0, 116.6, 117.8, 127.2, 128.2, 128.6, 132.6, 134.9, 135.7, 149.3, 151.8; Analysis: C17H15NO2 requires C, 76.96; H, 5.70; N, 5.28. found C, 76.91; H, 5.67; N, 5.27%.

Example 19

6-Vinylbenzo[d][1,3]dioxole-5-carbonitrile (Iv): (Substituted 2-bromobenzaldehydes: 2-bromo pipernal)

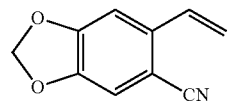

Yield: 88% (for two steps), colorless solid; mp 88-91° C.; IR (CHCl3): 756, 868, 930, 1038, 1162, 1263, 1359, 1486, 1505, 1604, 1615, 2219, 2916, 3018 cm-1; 1H NMR (200 MHz, CDCl3): 5.44 (d, J=11.10 Hz, 1H), 5.77 (d, J=17.36 Hz, 1H), 6.07 (s, 2H), 6.95-7.04 (m, 2H), 7.09 (s, 1H); 13C NMR (CDCl3): δ 102.3, 104.0, 104.8, 110.9, 117.2, 117.7, 132.5, 137.5, 147.4, 151.8; Analysis: C10H7NO2 requires C, 69.36; H, 4.07; N, 8.09. found C, 69.34; H, 4.02; N, 7.99%.

Experimental Procedure for the Preparation of Cyano Stilbene (Ix and y)

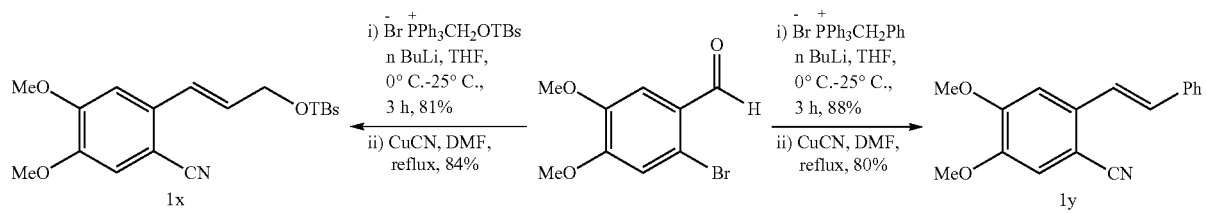

To a stirred solution of benzyl triphenylphosphonium Bromide (1.05 eq) (for Iy) or methyleneOTBs triphenylphosphonium Bromide (1.05 eq) in THF was added n-butyl lithium in hexane (1.05 eq), the solution was stirred for 30 min at 0° C. and substituted 2-bromo benzaldehydes (1.0 eq) in THF was added drop wise via syringe at the same temperature and the reaction mixture was allowed to stir for 3 h at room temperature (monitored by TLC). The reaction mixture was cooled to 0° C., followed by dilution with sat. NH4Cl (25 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (90:10) as an eluent] gave 2-bromostyrenes in 81 and 88% yield. The product was taken in dry DMF (20 mL) and CuCN (15.6 mmol) was added and refluxed under N2 for 18 h (monitored by TLC). The reaction mixture was cooled to room temperature, diluted with water (30 mL) and EtOAc (25 mL). The organic layer was separated and the aqueous layer was extracted with EtOAc (2×20 mL). The combined organic extracts were washed with brine and dried over anhyd.

Na2SO4 and concentrated under reduced pressure to give crude products which was purified by column chromatography [silica gel (230-400 mesh) and petroleum ether:EtOAc (70:30) as an eluent] gave Ix and Iy in 84 and 80% yield respectively.

Experimental Procedure for the Preparation of Cyano Stilbene (1W and Z)

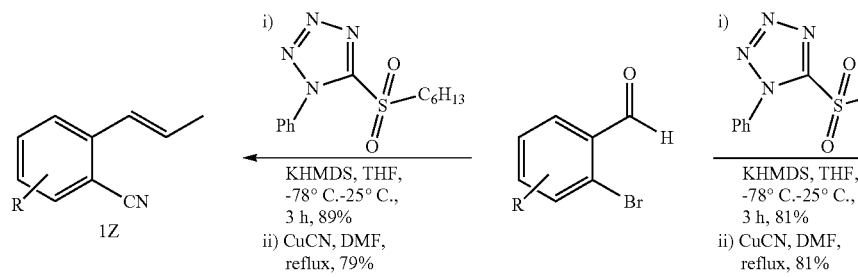
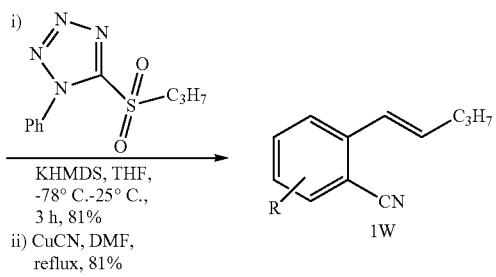

To a stirred solution of Substituted Suflone (1.0 eq) in THF was added KHMDS (1.1 eq), the solution was stirred for 30 min at −78° C. and substituted 2-bromo benzaldehydes (1.0 eq) in THF was added drop wise via syringe at the same temperature and the reaction mixture was allowed to stir for 3 h at room temperature (monitored by TLC). The reaction mixture was cooled to 0° C., followed by dilution with sat. NH$_4$Cl (25 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (95:5) as an eluent] gave 2-bromostyrenes in 81 and 89% yield. The product was taken in dry DMF (20 mL) and CuCN (15.6 mmol) was added and refluxed under N2 for 18 h (monitored by TLC). The reaction mixture was cooled to room temperature, diluted with water (30 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (75:25) as an eluent] gave Iw and Iz in 81 and 79% yield respectively.

Example 20

4,5-Dimethoxy-2-styrylbenzonitrile (1y): (substituted 2-bromobenzaldehydes: 4,5-dimethoxy, 2-bromo benzaldehyde)

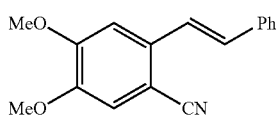

Yield: 83% (for two steps), colorless solid; mp 158-159° C.; IR (CHCl3): 696, 761, 1149, 1204, 1326, 1462, 1571, 1594, 2215, 2984, 3023 cm-1; 1H NMR (200 MHz, CDCl3): 3.91 (s, 3H), 4.01 (s, 3H), 7.01-7.17 (m, 3H), 7.26-7.42 (m, 4H), 7.54 (d, J=6.91 Hz, 2H); 13C NMR (CDCl3): δ 55.9, 102.9, 106.8, 113.6, 118.0, 123.8, 126.7, 128.7, 128.6, 131.2, 134.9, 136.1, 148.5, 152.6; Analysis: C17H15NO2 requires C, 76.96, H, 5.70; N, 5.28. found C, 76.89; H, 5.57; N, 5.19%.

Example 21

(E)-Ethyl 3-(3-cyanophenyl)acrylate (6)

To a stirred solution of 3-bromobenzaldehyde (50 mmol) in benzene (100 mL), Ph$_3$P=CHCO$_2$Et (55 mmol) was added. It was refluxed for 4 h under N$_2$ atmosphere. After the completion of reaction, benzene was distilled out to give the crude product, which was purified by column chromatography [silica gel (230-400 mesh) and petroleum ether:Ethyl acetate (90:10) as eluent] to afford pure product 3-bromo-ethyl cinnamates. The product was taken in dry DMF (20 mL) and CuCN (15.6 mmol) was added and refluxed under N$_2$ for 18 h (monitored by TLC). The reaction mixture was cooled to room temperature, diluted with water (30 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (70:30) as an eluent] gave 2-cyano-ethyl cinnamate in 93% yield.

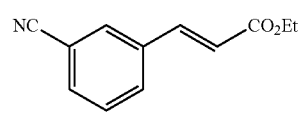

Yield: 93%; colorless solid; mp 62-65° C.; IR (CHCl3): 710, 765, 977, 1032, 1185, 1278, 1318, 1447, 1480, 1640, 1712, 2225, 2938, 2983 cm-1; 1H NMR (200 MHz, CDCl3): δ 1.35 (d, J=7.06 Hz, 3H), 4.28 (d, J=7.06 Hz, 2H), 6.48 (d, J=16.11 Hz, 1H), 7.48-7.80 (m, 5H); 13C NMR (CDCl3): δ 14.1, 60.5, 113.2, 117.8, 120.8, 129.6, 131.1, 131.6, 132.8, 135.5, 141.5, 165.7; Analysis: C12H11NO2 requires C, 71.63; H, 5.51; N, 6.96. found C, 71.59; H, 5.45; N, 6.85%.

Example 22

(E)-Ethyl 3-(4-cyanophenyl)acrylate (7)

To a stirred solution of 4-bromobenzaldehyde (50 mmol) in benzene (100 mL), Ph$_3$P=CHCO$_2$Et (55 mmol) was added. It was refluxed for 4 h under N$_2$ atmosphere. After the completion of reaction, benzene was distilled out to give the crude product, which was purified by column chromatography [silica gel (230-400 mesh) and petroleum ether:Ethyl acetate (90:10) as eluent] to afford pure product 4-bromoethyl cinnamates. The product was taken in dry DMF (20 mL) and CuCN (15.6 mmol) was added and refluxed under $N_2$ for 18 h (monitored by TLC). The reaction mixture was cooled to room temperature, diluted with water (30 mL) and EtOAc (25 mL). The organic layer was separated and the aqueous layer was extracted with EtOAc (2×20 mL). The combined organic extracts were washed with brine and dried over anhyd. Na2SO4 and concentrated under reduced pressure to give crude products which was purified by column chromatography [silica gel (230-400 mesh) and petroleum ether:EtOAc (70:30) as an eluent] gave 2-cyano-ethyl cinnamate in 93% yield.

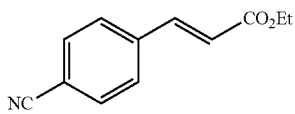

7

Yield: 93%; colorless solid; mp 68-70° C.; IR (CHCl3): 730, 795, 955, 1065, 1194, 1268, 1375, 1445, 1495, 1652, 1721, 2226, 2983 cm-1; 1H NMR (200 MHz, CDCl3): δ 1.35 (d, J=7.15 Hz, 3H), 4.28 (d, J=7.15 Hz, 2H), 6.51 (d, J=15.85 Hz, 1H), 7.59-7.71 (m, 5H); 13C NMR (CDCl3): δ 14.1, 60.6, 113.2, 117.9, 121.6, 128.2, 132.4, 138.5, 141.8, 165.7; Analysis: C12H11NO2 requires C, 71.63; H, 5.51; N, 6.96. found C, 71.58; H, 5.48; N, 6.88%.

Example 23

(2S,3R)-Ethyl 3-(3-cyanophenyl)-2,3-dihydroxypropanoate (8)

To a 250 mL RB flask was charged $K_3Fe(CN)_6$ (30 mmol), $K_2CO_3$ (30 mmol), tert-BuOH (25 mL), THF (25 mL) and $H_2O$ (50 mL). Reaction mixture was stirred for 10 min and (DHQD)2-PHAL (1 mol %) and $K_2OsO_4$ (0.5 mol %) were added and stirred for additional 30 min. To the reaction mixture 6 was added and allowed to stir for 24 h at 25° C. After completion of reaction, sodium bisulphate (5 g) was added slowly at 0° C. Organic layer was separated and aqueous layer was extracted with ethyl acetate (3×50 ml) combined organic layer was washed with brine (100 mL), dried over sodium sulphate and concentrated under reduced pressure to yield the crude products, Flash column chromatography purification [silica gel (230-400 mesh) and petroleum ether:EtOAc (70:30) as an eluent] afforded 8 in pure form.

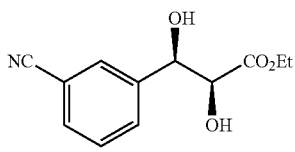

8

Yield: 93%; Gum; [α]D25–36.06 (c 1.20, CHCl3); IR (CHCl3): 680, 725, 954, 1057, 1118, 1214, 1291, 1734, 2229, 2985, 3443 cm-1; 1H NMR (200 MHz, CDCl3): δ 1.30 (d, J=7.16 Hz, 3H), 3.26 (d, J=7.51 Hz, 1H), 3.43 (d, J=5.89 Hz, 1H), 4.24-4.34 (m, 3H), 5.02 (dd, J=2.38, 7.51 Hz, 1H), 7.49 (d, J=7.52 Hz, 1H), 7.57-7.67 (m, 2H), 7.72 (s, 1H); 13C NMR (CDCl3): δ 14.1, 62.3, 73.5, 74.5, 112.2, 118.6, 129.0, 130.2, 130.9, 131.3, 141.9, 172.3; Analysis: C12H13NO4 requires C, 61.27; H, 5.57; N, 5.95. found C, 61.26; H, 5.54; N, 5.89.

Example 24

(2S,3R)-Ethyl 3-(4-cyanophenyl)-2,3-dihydroxypropanoate (9)

To a 250 mL RB flask was charged $K_3Fe(CN)_6$ (30 mmol), $K_2CO_3$ (30 mmol), tert-BuOH (25 mL), THF (25 mL) and $H_2O$ (50 mL). Reaction mixture was stirred for 10 min and (DHQD)2-PHAL (1 mol %) and $K_2OsO_4$ (0.5 mol %) were added and stirred for additional 30 min. To the reaction mixture 7 was added and allowed to stir for 24 h at 25° C. After completion of reaction, sodium bisulphate (5 g) was added slowly at 0° C. Organic layer was separated and aqueous layer was extracted with ethyl acetate (3×50 ml) combined organic layer was washed with brine (100 mL), dried over sodium sulphate and concentrated under reduced pressure to yield the crude products, Flash column chromatography purification [silica gel (230-400 mesh) and petroleum ether:EtOAc (70:30) as an eluent] afforded 9 in pure form.

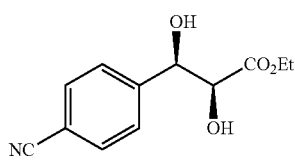

9

Yield: 93%; colorless solid; mp 102-103° C.; [α]D25–36.42 (c 1.10, CHCl3); IR (CHCl3): 685, 765, 1017, 1050, 1105, 1204, 1257, 1752, 2228, 2978, 3332 cm-1; 1H NMR (200 MHz, CDCl3): δ 1.31 (d, J=7.06 Hz, 3H), 3.03 (d, J=7.63 Hz, 1H), 3.27 (d, J=5.36 Hz, 1H), 4.24-4.35 (m, 3H), 5.05 (dd, J=2.38, 7.51 Hz, 1H), 7.49 (d, J=7.52 Hz, 1H), 7.57-7.67 (m, 2H), 7.72 (s, 1H); 13C NMR (CDCl3+ CD3OD): δ 12.9, 60.6, 73.2, 74.2, 110.0, 117.9, 126.7, 131.0, 146.2, 171.4; Analysis: C12H13NO4 requires C, 61.27; H, 5.57; N, 5.95. found C, 61.23; H, 5.52; N, 5.84%.

Example 25

Preparation of Benzyl(1R,2S)-2-(ethoxycarbonyl)-1-(2-cyanophenyl)-2-hydroxyethylcarbamate (12)

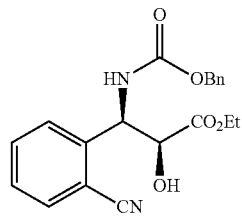

12

Sodium hydroxide (60 mg, 1.5 mmol) was dissolved in water (4 mL), and 0.5 mL of this NaOH solution was transferred to a small vial containing K2OsO2(OH)4 (0.020 mmol for 4 mol %) for later use. To the remainder of the NaOH solution were added the carbamate (1.55 mmol) and n-PrOH (2 mL). The mixture was stirred for 2 min and placed in a water bath before tert-butylhypochlorite16 (175 L, 1.52 mmol) was slowly added with vigorous stirring. Then, the resulting solution was sequentially treated with a solution of (DHQD)2PHAL (0.025 mmol for 5 mol %) in n-PrOH (1 mL), the o-cyano ethylcinnamate (0.50 mmol), the previously prepared solution of K2OsO2(OH)4, and n-PrOH (1 mL). The reaction mixture was monitored by TLC to establish completion, quenched by the addition of saturated aqueous sodium sulfite (4 mL) while being cooled in an ice-water bath, and stirred for an additional 30 min. The separated aqueous phase was extracted with EtOAc (3×5 mL), and the combined organic extracts were washed with water (3 mL) followed by brine (5 mL), dried over Na2SO4, and concentrated under reduced pressure to give crude products which was purified by column chromatography [silica gel (230-400 mesh) and petroleum ether:EtOAc (60:40) as an eluent] gave product 10 in 64% yield with dr 6:1.Gum; [α]D25−36.06 (c 1.10, CHCl3); IR (CHCl3): 756, 857, 974, 1037, 1095, 1184, 1202, 1275, 1291, 1319, 1347, 1368, 1393, 1477, 1573, 1607, 1640, 1716, 2219, 2984, 3023, 3415 cm-1; $^1$H NMR (200 MHz, CDCl3): δ 1.28 (t, J=7.16 Hz, 3H), 3.34 (d, J=7.51 Hz, 1H), 4.29 (q, J=7.16 Hz, 2H), 4.50 (s, 1H), 5.06 (dd, J=2.38, 7.51 Hz, 1H), 5.62 (d, J=8.9 Hz, 1H), 5.85 (d, J=8.9 Hz, 1H), 7.32-7.36 (m, 5H), 7.39-7.56 (m, 3H), 7.66-7.77 (m, 1H); $^{13}$C NMR (CDCl3): δ 14.2, 55.3, 60.3, 62.8, 72.5, 111.1, 117.0, 122.0, 128.4, 132.8, 133.2, 142.9, 145.8, 155.3, 172.0; Analysis: C12H13NO4 requires C, 61.27; H, 5.57; N, 5.95. found C, 61.26; H, 5.54; N, 5.89.

Example 26

Ethyl 2-(1,3-dihydro-1-iminoisobenzofuran-3-yl)-2-hydroxyacetate (15a): (Intermediate)

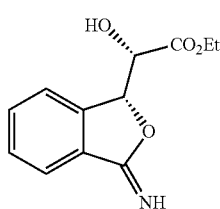

IR (CHCl3): 687, 728, 975, 1050, 1320, 1385, 1468, 1498, 1678, 1758, 2874, 2958, 3413 cm-1; 1H NMR (200 MHz, CDCl3): δ 1.29 (t, J=6.85 Hz, 3H), 4.29 (d, J=6.85 Hz, 2H), 4.73 (d, J=2.33 Hz, 1H), 6.10 (s, 1H), 7.59 (t, J=6.60 Hz, 2H), 7.75 (t, J=6.60 Hz, 1H), 7.92 (d, J=8.48 Hz, 1H); 13C NMR (CDCl3): δ 12.4, 60.9, 69.4, 88.2, 121.5, 123.8, 128.2, 128.9, 134.1, 144.4, 167.8, 169.6; ESI-MS: m/z 235.01[M+Na]+.

Example 27

2,4-Dimethoxy-6-styrylbenzonitrile (17)

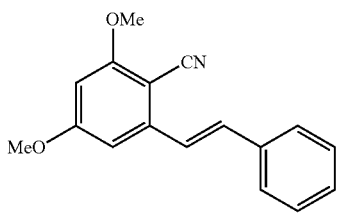

Yield: 79%; colorless solid; mp 147-148° C.; IR (CHCl3): 694, 831, 953, 1045, 1073, 1150, 1203, 1326, 1460, 1570, 1595, 2216 cm-1; 1H NMR (400 MHz, CDCl3): δ 3.90 (s, 6H), 6.34 (d, J=2.3 Hz, 1H), 6.80 (d, J=2.3 Hz, 1H), 7.20 (d, J=16.4 Hz, 1H), 7.26-7.30 (m, 1H), 7.32-7.38 (m, 3H), 7.55 (d, J=7.38 Hz, 2H); 13C NMR (CDCl3): δ 55.6, 56.0, 94.1, 97.4, 101.4, 115.7, 124.4, 127.2, 128.8, 133.5, 136.1, 143.4, 163.2, 163.9; Analysis: C17H15NO2 requires C, 76.96; H, 5.70; N, 5.28. found C, 76.92; H, 5.68; N, 5.24%.

Example 28

2,4-Dimethoxy-6-((E)-prop-1-enyl)-benzonitrile (16)

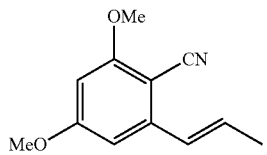

Yield: 72%; Gum; IR (CHCl3): 720, 857, 9662, 1036, 1092, 1129, 1260, 1318, 1381, 1386, 1450, 1576, 1616, 1629, 1647, 2216, 2982, 3030 cm-1; 1H NMR (200 MHz, CDCl3): δ 1.95 (d, J=6.4 Hz, 3H), 3.86 (s, 3H), 3.89 (s, 3H), 6.29-6.30 (m, 1H), 6.39-6.46 (m, 1H), 6.60 (d, J=1.8 Hz, 1H), 6.69 (d, J=15.5 Hz, 1H); 13C NMR (CDCl3): δ 18.7, 55.5, 55.9, 96.8, 101.5, 106.4, 115.7, 126.6, 127.6, 131.4, 144.1, 163.1, 163.8; Analysis: C12H13NO2 requires C, 70.92; H, 6.45; N, 6.89. found C, 70.89; H, 6.40; N, 6.85%.

Example 29

Preparation of (S)-Ethyl-2-((R)-1,3-dihydro-1-oxoisobenzofuran-3-yl)-2-hydroxyacetate (IIa)

To a 250 mL RB flask was charged $K_3Fe(CN)_6$ (30 mmol), $K_2CO_3$ (30 mmol), $MeSO_2NH_2$ (10 mmol), tert-BuOH (25 mL), THF (25 mL) and $H_2O$ (50 mL). Reaction mixture was stirred for 10 min and $(DHQD)_2$-PHAL (1 mol %) and $K_2OsO_4$ (0.5 mol %) were added and stirred for additional 30 min. To the reaction mixture I a was added and allowed to stir for 7 h at 25° C. After completion of reaction, sodium bisulphate (5 g) was added slowly at 0° C. Organic layer was separated and aqueous layer was extracted with ethyl acetate (3×50 ml) combined organic layer was washed with brine (100 mL), dried over sodium sulphate and concentrated under reduced pressure to yield the crude products, Flash column chromatography purification [silica gel (230-400 mesh) and petroleum ether:EtOAc (60:40) as an eluent] afforded II a in pure form.

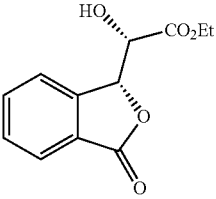

Yield: 94%, colorless solid; mp 146-148° C.; 99% ee by chiral HPLC analysis (Chiracel OJ-H, n-hexane-iPrOH, 90:10, 0.5 mL min-1) retention time 12.16 (99.65%) and 13.80 (0.35%); [α]D$^{25}$ −95.65 (c 1.24, CHCl3); IR (CHCl3): 762, 856, 968, 1027, 1068, 1078, 1210, 1298, 1349, 1467, 1611, 1652, 1720, 1768, 2924, 3014, 3440 cm-1; $^1$H NMR (200 MHz, CDCl3): δ 1.29 (t, J=7.17 Hz, 3H), 3.16 (d, J=5.79 Hz, 1H), 4.30 (q, J=7.17 Hz, 2H), 4.66 (dd, J=2.12, 5.81 Hz, 1H), 5.79 (d, J=2.12 Hz, 1H), 7.57 (t, J=7.06 Hz, 2H), 7.68-7.75 (m, 1H), 7.90-7.93 (m, 1H); 13C NMR (CDCl3): δ 13.8, 62.4, 70.3, 80.4, 122.0, 125.3, 126.4, 129.3, 134.0, 145.7, 169.82, 170.7; HRMS (ESI) calcd for C12H12O5 [M+H]+ 237.0763. found 237.0772.

Example 30

(S)-Ethyl-2-((R)-1,3-dihydro-5-methoxy-1-oxoisobenzofuran-3-yl)-2-hydroxyacetate (IIb)

Yield: 95%; colorless solid; mp 121-122° C.; 99% ee by chiral HPLC analysis (Chiracel OJ-H, n-hexane-iPrOH, 90:10, 1 mL min-1) retention time 25.80 (99.55%) and 30.33 (0.45%); [α]D25−94.49 (c 1.15, CHCl3); IR(CHCl3): 724, 876, 1031, 1084, 1191, 1212, 1278, 1295, 1357, 1398, 1445, 1486, 1578, 1607, 1721, 1765, 2984, 3023, 3415 cm-1; 1H NMR (200 MHz, CDCl3): δ 1.29 (t, J=7.20 Hz, 3H), 3.14 (brs, 3H), 3.91 (s, 3H), 4.29 (q, J=7.20 Hz, 2H), 4.63 (d, J=1.74 Hz, 1H), 5.69 (d, J=2.29 Hz, 1H), 6.96 (d, J=2.11 Hz, 1H), 7.05 (dd, J=2.11, 8.66 Hz, 1H), 7.80 (d, J=8.66 Hz, 1H); 13C NMR (CDCl3): δ 14.0, 55.8, 62.7, 70.5, 79.6, 106.0, 117.0, 118.9, 127.1, 148.5, 164.8, 169.5, 170.9; HRMS (ESI) calcd for C13H14O6 [M+H]+ 267.0869. found 267.0863.

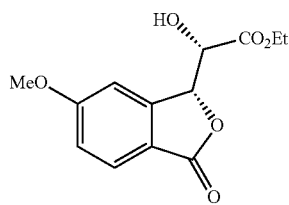

Example 31

(S)-Ethyl-2-((R)-1,3-dihydro-5,6-dimethoxy-1-oxoisobenzofuran-3-yl)-2-hydroxyacetate (IIc)

Yield: 94%; colorless solid; mp 144-146° C.; 99% ee by chiral HPLC analysis (Chiracel OJ-H, n-hexane-iPrOH, 90:10, 0.5 mL min-1) retention time 23.18 (99.36%) and 27.60 (0.64%); [α]D 25−95.12 (c 1.12, CHCl3); IR (CHCl3): 758, 945, 1125, 1297, 1507, 1722, 1764, 2925, 3010, 3341 cm-1; 1H NMR (200 MHz, CDCl3): δ 1.30 (t, J=7.20 Hz, 3H), 3.20 (d, J=6.23 Hz, 1H), 3.94 (s, 3H), 3.98 (s, 3H), 4.29 (q, J=7.25 Hz, 2H), 4.62 (dd, J=2.42, 6.16 Hz, 1H), 5.66 (d, J=2.20 Hz, 1H), 6.93 (s, 1H), 7.27 (s, 1H); 13C NMR (DMSOd6): δ 14.4, 56.2, 56.4, 61.2, 70.2, 81.2, 105.2, 105.8, 118.2, 141.7, 150.5, 154.8, 170.2, 171.3; HRMS (ESI) calcd for C14H16O7 [M+H]+ 297.0974. found 297.0979.

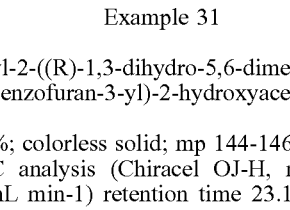

Example 32

(S)-Ethyl-2-((R)-1,3-dihydro-6,7-dimethoxy-1-oxoisobenzofuran-3-yl)-2-hydroxyacetate (IId)

Yield: 94%, colorless solid; m.p 110-112° C.; 99% ee by chiral HPLC analysis (Chiracel OJ-H, n-hexane-iPrOH, 90:10, 0.5 mL min-1) retention time 23.90 (99.44%) and 27.87 (0.56%); [α]D 25-95.28 (c 1.0, CHCl3); IR (CHCl3): 762, 946, 1132, 1298, 1518, 1728, 1764, 2985, 3034, 3425 cm-1; 1H NMR (200 MHz, CDCl3): δ 1.30 (t, J=7.19 Hz, 3H), 3.19 (brs, 1H), 3.91 (s, 3H), 4.10 (s, 3H), 4.29 (q, J=7.19 Hz, 2H), 4.57 (s, 1H), 5.65 (d, J=2.09 Hz, 1H), 7.13 (d, J=8.11 Hz, 1H), 7.23 (d, J=8.11 Hz, 1H); 13C NMR (CDCl3): δ 14.1, 56.7, 62.2, 62.6, 70.7, 79.0, 116.4, 118.8, 119.3, 138.5, 148.4, 152.9, 167.2, 170.9; HRMS (EST) calcd for C14H16O7 [M+H]+ 297.0974. found 297.0979.

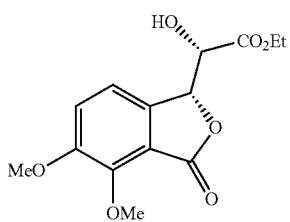

Example 33

(S)-Ethyl-2-((R)-1,3-dihydro-5,7-dimethoxy-1-oxoisobenzofuran-3-yl)-2-hydroxyacetate (IIe)

Yield: 94%, colorless solid; mp 154-156° C.; 99% ee by chiral HPLC analysis (Chiracel OJ-H, n-hexane-iPrOH, 90:10, 0.5 mL min-1) retention time 18.37 (99.60%) and 21.74 (0.40%); [α]D 25−96.29 (c 1.15, CHCl3); IR (CHCl3): 746, 985, 1130, 1287, 1514, 1723, 1762, 2954, 3085, 3414 cm-1; 1H NMR (200 MHz, CDCl3): δ 1.32 (t, J=7.22 Hz, 3H), 3.37 (brs, 1H), 3.91 (s, 3H), 3.94 (s, 3H), 4.30 (q, J=7.22 Hz, 2H), 4.61 (s, 1H), 5.67 (s, 1H), 6.47 (s, 1H), 6.59 (s, 1H); 13C NMR (CD3OD): δ 14.6, 56.5, 56.9, 63.0, 71.9, 82.1, 99.9, 100.3, 108.1, 153.1, 160.9, 168.9, 170.6, 172.5; HRMS (ESI) calcd for C14H16O7 [M+H]+ 297.0974. found 297.0979.

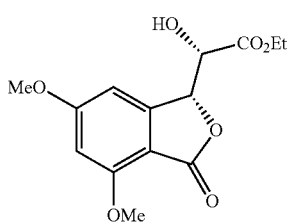

Example 34

(S)-Ethyl-2-((R)-1,3-dihydro-5,6,7-trimethoxy-1-oxoisobenzofuran-3-yl)-2-hydroxyacetate (IIf)

Yield: 92%, colorless solid; mp 111-112° C.; [α]D 25−94.65 (c 1.23, CHCl3); IR (CHCl3): 1012, 1094, 1140, 1254, 1350, 1475, 1602, 1765, 2954, 3085, 3408 cm-1; 1H NMR (200 MHz, CDCl3): δ 1.31 (t, J=7.20 Hz, 3H), 3.09 (s, 1H), 3.86 (s, 3H), 3.96 (s, 3H), 4.13 (s, 3H), 4.31 (q, J=7.20 Hz, 2H), 4.58 (d, J=2.16 Hz, 1H), 5.58 (d, J=2.16 Hz, 1H), 6.70 (s, 1H); 13C NMR (CDCl3): δ 13.9, 56.3, 61.1, 62.0, 62.4, 79.1, 99.6, 111.0, 142.0, 143.5, 152.1, 159.7, 167.3, 176.8; HRMS (ESI) calcd for C15H18O8 [M+H]+ 327.1080. found 327.1072.

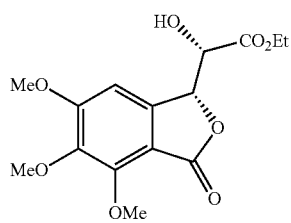

II f

Example 35

(S)-Ethyl-2-((R)-5-(p-toluenesulfonoyloxy)-1,3-dihydro-6-methoxy-1-oxoisobenzofuran-3-yl)-2-hydroxyacetate (IIg)

Yield: 93%, colorless solid; mp 107-108° C.; [α]D 25−94.89 (c 1.15, CHCl3); IR (CHCl3): 768, 819, 1025, 1050, 1120, 1180, 1190, 1330, 1374, 1494, 1614, 1767, 2924, 3012, 3371 cm-1; 1H NMR (200 MHz, CDCl3): δ 1.27 (t, J=7.20 Hz, 3H), 2.48 (s, 3H), 3.07 (s, 1H), 3.78 (s, 3H), 4.26 (q, J=7.20 Hz, 2H), 4.63 (d, J=2.16 Hz, 1H), 5.67 (d, J=2.16 Hz, 1H), 6.99 (s, 1H), 7.35 (d, J=8.14 Hz, 2H), 7.49 (s, 1H), 7.76 (d, J=8.14 Hz, 2H); 13C NMR (DMSO-d6): δ 14.5, 21.8, 56.7, 61.4, 70.3, 71.6, 84.1, 107.4, 118.7, 119.7, 128.6, 130.1, 132.6, 139.5, 145.9, 147.9, 157.0, 168.8, 170.9; HRMS (ESI) calcd for C20H20O9S [M+H]+ 437.0906. found 437.0912.

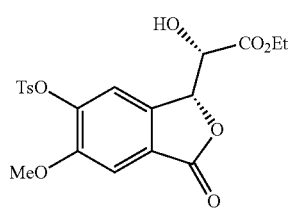

II g

Example 36

(S)-Ethyl-2-((R)-5-(benzyloxy)-1,3-dihydro-6-methoxy-1-oxoisobenzofuran-3-yl)-2-hydroxyacetate (IIh)

Yield: 94%, colorless solid; mp 138-140° C.; [α]D 25−96.04 (c 1.21, CHCl3); IR (CHCl3): 738, 856, 1025, 1078, 1130, 1184, 1195, 1336, 1395, 1494, 1645, 1765, 2942, 3035, 3413 cm-1; 1H NMR (200 MHz, CDCl3): δ 1.28 (t, J=7.05 Hz, 3H), 3.04 (d, J=5.93 Hz, 1H), 3.94 (s, 3H), 4.27 (q, J=7.05 Hz, 2H), 4.55 (dd, J=2.59, 5.93 Hz, 1H), 5.22 (d, J=3.59 Hz, 2H), 5.61 (d, J=2.08 Hz, 1H), 6.94 (s, 1H), 7.26 (s, 1H), 7.29-7.45 (m, 5H); 13C NMR (DMSO-d6): δ 13.7, 55.7, 61.5, 70.3, 70.6, 79.9, 105.2, 105.8, 118.5, 127.0, 127.8, 128.3, 135.3, 139.9, 150.8, 153.6, 169.7, 170.4; HRMS (ESI) calcd for C20H20O7 [M+H]+ 373.1287. found 373.1293.

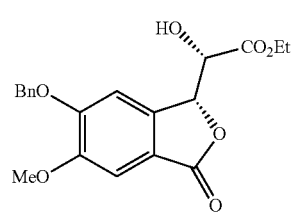

II h

Example 37

(S)-Ethyl-2-((R)-5-1,3-dihydro-5,6-dioxomethyl-1-oxoisobenzofuran-3-yl)-2-hydroxyacetate (II k)

Yield: 95%, colorless solid; mp 150-153° C.; [α]D25−95.74 (c 1.0, CHCl3); IR (CHCl3): 786, 891, 1015, 1054, 1122, 1183, 1196, 1356, 1395, 1489, 1618, 1755, 2942, 3021, 3410 cm-1; 1H NMR (200 MHz, CDCl3): δ 1.31 (t, J=7.14 Hz, 3H), 3.10 (brs, 1H), 4.30 (qd, J=1.40, 7.14 Hz, 2H), 4.56 (s, 1H), 5.62 (d, J=2.19 Hz, 1H), 6.14 (dd, J=1.40, 4.44 Hz, 2H), 6.89 (s, 1H), 7.20 (s, 1H); 13C NMR (CDCl3): δ 14.0, 62.6, 70.4, 79.6, 101.9, 102.7, 104.3, 120.4, 142.2, 149.6, 153.7, 169.3, 170.8; Analysis: C13H12O7 requires C, 55.72; H, 4.32. found C, 55.65; H, 4.29%.

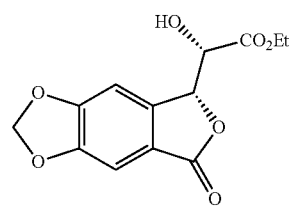

II k

Example 38

(S)-Ethyl 2-((R)-1,3-dihydro-1-oxonaphtho[2,1-c]furan-3-yl)-2-hydroxyl acetate (II l)

Yield: 94%, colorless solid; mp 107-109° C.; [α]D 25−95.69 (c 1.15, CHCl3); IR (CHCl3): 784, 865, 989, 1010, 1106, 1210, 1275, 1291, 1319, 1368, 1573, 1607, 1750, 2978, 3084, 3457 cm-1; 1H NMR (200 MHz, CDCl3): δ 1.28 (t, J=7.45 Hz, 3H), 3.14 (d, J=6.06 Hz, 1H), 4.31 (q, J=7.45 Hz, 2H), 4.74 (dd, J=2.14, 6.06 Hz, 1H), 5.85 (d, J=2.14 Hz, 1H), 7.58 (d, J=8.50 Hz, 1H), 7.63-7.78 (m, 2H), 7.97 (d, J=8.5 Hz, 1H), 8.16 (d, J=8.5 Hz, 1H) 8.97 (d, J=8.5 Hz, 1H); 13C NMR (CDCl3+CD3OD): δ 13.2, 61.5, 69.8, 80.3, 118.2, 118.6, 120.3, 122.4, 126.8, 128.0, 128.4, 133.0, 135.2, 147.6, 170.4; Analysis: C16H14O5 requires C, 67.13; H, 4.93. found C, 67.11; H, 4.89%.

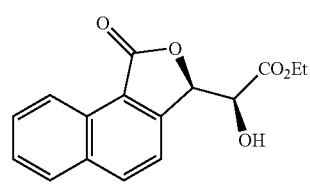

II l

Example 39

(R)-3-(Hydroxymethyl)isobenzofuran-1(3H)-one (II m)

To a 250 mL RB flask was charged $K_3Fe(CN)_6$ (30 mmol), $K_2CO_3$ (30 mmol), tert-BuOH (25 mL), THF (25 mL) and $H_2O$ (50 mL). Reaction mixture was stirred for 10 min and $(DHQD)_2$-PHAL (1 mol %) and $K_2OsO_4$ (0.5 mol %) were added and stirred for additional 30 min. To the reaction mixture Im was added and allowed to stir for 5 h at 25° C. After completion of reaction, sodium bisulphate (5 g) was added slowly at 0° C. Organic layer was separated and aqueous layer was extracted with ethyl acetate (3×50 ml) combined organic layer was washed with brine (100 mL), dried over sodium sulphate and concentrated under reduced pressure to yield the crude products, Flash column chromatography purification [silica gel (230-400 mesh) and petroleum ether:EtOAc (60:40) as an eluent] afforded II m in pure form.

Yield: 95%, colorless solid; mp 101-104° C.; 99% ee by chiral HPLC analysis (Chiracel OJ-H, n-hexane-iPrOH, 90:10, 0.5 mL min-1) retention time 8.03 (99.36%) and 9.24 (0.64%); [α]D25−78.12 (c 1.23, CHCl3); IR (CHCl3): 744, 847, 968, 1025, 1067, 1089, 1211, 1288, 1349, 1467, 1607, 1640, 1756, 2924, 3012, 3440 cm-1; 1H NMR (200 MHz, CDCl3): 2.61 (s, 1H), 3.90 (d, J=11.80 Hz, 1H), 4.14 (d, J=11.80 Hz, 1H), 5.54-5.59 (m, 1H), 7.55 (t, J=7.79 Hz, 2H), 7.70 (td, J=1.14, 7.42 Hz, 1H), 7.89 (d, J=7.42 Hz, 1H); 13C NMR (CDCl3+CD3OD): δ 61.7, 81.6, 121.6, 124.2, 125.6, 128.4, 133.4, 146.8, 170.6; HRMS (ESI) calcd for C9H8O3 [M+H]+ 165.0552. found 165.0559.

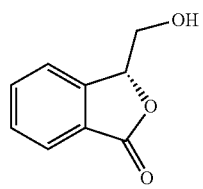

IIm

Example 40

(R)-3-(Hydroxymethyl)-5-methoxyisobenzofuran-1(3H)-one (II n)

Yield: 95%, colorless solid; mp 137-140° C.; 99% ee by chiral HPLC analysis (Chiracel OJ-H, n-hexane-iPrOH, 90:10, 1 mL min-1) retention time 27.19 (99.36%) and 39.72 (0.64%); [α]D 25−78.36 (c 1.12, CHCl3); IR (CHCl3): 728, 868, 1026, 1256, 1490, 1607, 1640, 1749, 2853, 2923, 3440 cm-1; 1H NMR (200 MHz, CDCl3): 2.31 (brs, 1H), 3.84-3.91 (m, 4H), 4.06-4.14 (m, 1H), 5.46 (t, J=5.30 Hz, 1H), 6.94 (d, J=2.0 Hz, 1H), 7.04 (dd, J=2.0, 8.60 Hz, 1H), 7.80 (d, J=8.60 Hz, 1H); 13C NMR (CDCl3+CD3OD): δ 54.9, 62.1, 81.1, 105.6, 116.4, 117.8, 126.1, 149.8, 164.5, 170.8; HRMS (ESI) calcd for: C10H10O4 [M+H]+ 195.0657. found 195.0663.

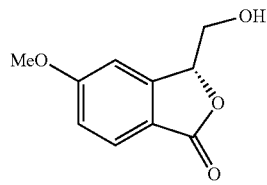

II n

Example 41

(R)-3-(Hydroxymethyl)-5,6-dimethoxyisobenzofuran-1(3H)-one (II o)

Yield: 93%, colorless solid; mp 165-167° C.; 99% ee by chiral HPLC analysis (Chiracel OJ-H, n-hexane-iPrOH, 90:10, 0.5 mL min-1) retention time 23.18 (99.36%) and 27.60 (0.64%); [α]D 25−77.89 (c 1.0, CHCl3); IR (CHCl3): 698, 828, 956, 102v7, 1056, 1225, 1266, 1309, 1335, 1474, 1508, 1612, 1752, 2922, 3023, 3358 cm-1; 1H NMR (200 MHz, CDCl3): 2.71 (t, J=6.44 Hz, 1H), 3.81-3.90 (m, 1H), 3.93 (s, 3H), 3.99 (s, 3H), 4.04-4.15 (m, 1H), 5.42-5.47 (m, 1H), 6.93 (s, 1H), 7.25 (s, 1H); 13C NMR (DMSO-d6): δ 56.1, 56.3, 62.4, 81.7, 105.0, 105.8, 117.9, 142.4, 150.4, 154.6, 170.6; HRMS (ESI) calcd for: C11H12O5 [M+H]+ 225.0763. found 225.0772.

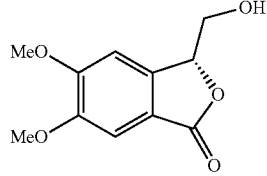

II o

Example 42

(R)-3-(Hydroxymethyl)-6,7-dimethoxyisobenzofuran-1(3H)-one (II p)

Yield: 94%, colorless solid; mp 85-88° C.; 99% ee by chiral HPLC analysis (Chiracel OJ-H, n-hexane-iPrOH, 90:10, 0.5 mL min-1) retention time 18.27 (99.36%) and 20.93 (0.64%); [α]D 25−78.21 (c 1.0, CHCl3); IR (CHCl3): 698, 798, 956, 1030, 1067, 1220, 1328, 1339, 1458, 1605, 1745, 2976, 3012, 3457 cm-1; 1H NMR (200 MHz, CDCl3): 2.24 (brs, 1H), 3.79-3.85 (m, 1H), 3.90 (s, 3H), 3.95 (s, 3H), 4.03-4.09 (m, 1H), 5.35-5.39 (m, 1H), 6.42 (s, 1H), 6.48 (s, 1H); 13C NMR (CDCl3): δ 56.6, 62.0, 63.7, 80.7, 116.8, 118.4, 119.4, 139.7, 148.0, 152.5, 168.2; HRMS (ESI) calcd for: C11H12O5 [M+H]+

225.0718. found 225.0715. HRMS (ESI) calcd for: C11H12O5[M+H]+ 225.0763. found 225.0772.

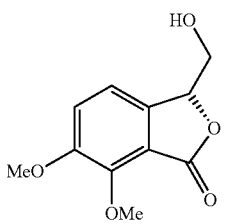

Example 43

(R)-3-(Hydroxymethyl)-5,7-dimethoxyisobenzofuran-1(3H)-one (II q)

Yield: 94%, colorless solid; mp 152-153° C.; 99% ee by chiral HPLC analysis (Chiracel OJ-H, n-hexane-iPrOH, 90:10, 0.5 mL min-1) retention time 18.27 (99.36%) and 20.40 (0.64%); [α]D 25−78.11 (c 1.0, CHCl3); IR (CHCl3): 695, 765, 950, 1030, 1058, 1232, 1331, 1365, 1463, 1615, 1751, 2982, 3010, 3443 cm-1; $^1$H NMR (200 MHz, CDCl3): 2.53 (brs, 1H), 3.77-3.88 (m, 1H), 3.91 (s, 3H), 3.99-4.04 (m, 3H), 4.10 (s, 1H), 5.40-5.45 (m, 1H), 7.09 (dd, J=084, 8.20 Hz, 1H), 7.22 (d, J=8.20 Hz, 1H); $^{13}$C NMR (CDCl3): δ 54.7, 54.9, 62.2, 80.4, 97.6, 98.2, 105.9, 151.7, 158.9, 166.6, 168.9; HRMS (ESI) calcd for: C11H12O5 [M+H]+ 225.0763. found 225.0772.

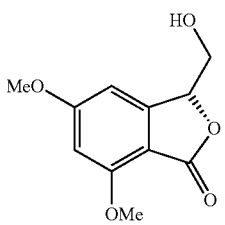

Example 44

(R)-3-(Hydroxymethyl)-5,6,7-trimethoxyisobenzofuran-1(3H)-one (II r)

Yield: 92%, colorless solid; mp 178-180° C.; [α]D25−78.05 (c 1.15, CHCl3); IR (CHCl3): 1014, 1097, 1254, 1345, 1483, 1600, 1754, 2947, 3017, 3444 cm-1; $^1$H NMR (200 MHz, CDCl3): 2.62 (brs, 1H), 3.84-3.90 (m, 4H), 3.96 (s, 3H), 4.03-4.09 (m, 1H), 4.13 (s, 3H), 5.35-5.39 (m, 1H), 6.69 (s, 1H); $^{13}$C NMR (CDCl3+CD3OD): δ 56.4, 61.2, 62.1, 63.7, 80.6, 99.9, 110.7, 141.8, 144.8, 152.1, 159.7, 168.3; HRMS (ESI) calcd for: C12H14O6 [M+H]+ 255.0869. found 255.0863.

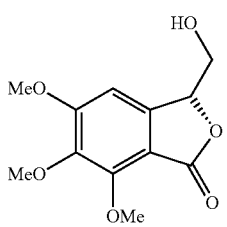

Example 45

(R)-1,3-Dihydro-1-(hydroxymethyl)-5-methoxy-3-oxoisobenzofuran-6-yl-4-methylbenzenesulfonate (II s)

Yield: 93%, colorless solid; mp 152-154° C.; [α]D 25−77.79 (c 1.18, CHCl3); IR (CHCl3): 734, 849, 973, 103, 1053, 1178, 1345, 1372, 1494, 1614, 1755, 2919, 3018, 3437 cm-1; $^1$H NMR (200 MHz, CDCl3): 2.24 (brs, 1H), 2.48 (s, 3H), 3.80 (s, 3H), 3.92 (dd, J=4.60, 12.36 Hz, 1H), 4.03 (dd, J=4.73, 12.36 Hz, 1H), 5.44 (t, J=4.60 Hz, 1H), 6.97 (s, 1H), 7.35 (d, J=8.28 Hz, 2H), 7.48 (s, 1H), 7.78 (d, J=8.28 Hz, 2H); $^{13}$C NMR (CDCl3+CD3OD): δ 20.1, 55.1, 61.5, 81.0, 105.4, 117.4, 119.3, 127.7, 128.8, 131.9, 138.9, 145.2, 147.8, 156.6, 169.5; HRMS (ESI) calcd for: C17H16O7S [M+H]+ 365.0695. found 365.0693.

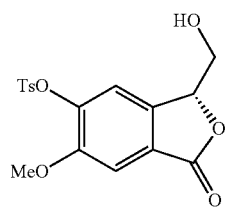

Example 46

(R)-5-(Benzyloxy)-3-(hydroxymethyl)-6-methoxyisobenzofuran-1(3H)-one (II t)

Yield: 94%, colorless solid; mp 126-128° C.; [α]D 25−78.22 (c 1.10, CHCl3); IR (CHCl3): 689, 825, 975, 1025, 1076, 1223, 1268, 1312, 1334, 1494, 1528, 1621, 1752, 2924, 3032, 3385 cm-1; $^1$H NMR (200 MHz, CDCl3): 2.31 (brs, 1H), 3.75-3.85 (m, 1H), 3.92 (s, 3H), 3.98-4.06 (m, 1H), 5.22 (s, 2H), 5.36-5.41 (m, 1H), 6.92 (s, 1H), 7.28 (s, 1H), 7.32-7.45 (m, 5H); $^{13}$C NMR (CDCl3): δ 56.2, 64.1, 71.1, 81.0, 105.4, 106.6, 118.7, 127.3, 128.4, 128.8, 135.6, 140.9, 151.3, 154.0, 170.5; HRMS (ESI) calcd for: C17H16O5 [M+H]+ 301.1076. found 301.1072.

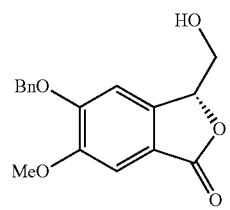

Example 47

(R)-3-(Hydroxymethyl)-5,6-dioxomethylisobenzofuran-1(3H)-one (II v)

Yield: 93%, colorless solid; mp 144-145° C.; [α]D 25−78.11 (c 1.20, CHCl3); IR (CHCl3): 698, 852, 957, 1024, 1067, 1232, 1286, 1319, 1343, 1484, 1582, 1612, 1766, 2942, 3054, 3389 cm-1; 1H NMR (200 MHz, CDCl3): 2.40 (brs, 1H), 3.84 (dd, J=4.05, 12.47 Hz, 1H), 4.06 (dd, J=4.05, 12.47 Hz, 1H), 5.41 (m, 1H), 6.13 (d, J=2.33 Hz, 2H), 6.87 (s, 1H), 7.20 (s, 1H); 13C NMR (DMSO-d6): δ 62.1, 81.3, 102.8, 103.3, 119.8, 144.5, 149.1, 153.3, 169.6;

HRMS (ESI) calcd for: C10H8O5 [M+H]+ 209.0450. found 209.0454.

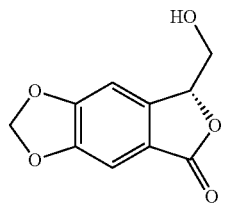

II v

Example 48

(R)-3-((R)-Hydroxy(phenyl)methyl)-5,6-dimethoxy-isobenzofuran-1(3H)-one (II y)

Yield: 94%, colorless solid; mp 113-115° C.; [α]D 25−79.23 (c 1.15, CHCl3); IR (CHCl3): 756, 857, 974, 1026, 1064, 1158, 1216, 1334, 1604, 1743, 2858, 2928, 3430 cm-1; 1H NMR (200 MHz, CDCl3): 3.05 (brs, 1H), 3.64 (s, 3H), 3.90 (s, 3H), 4.69 (d, J=7.44 Hz, 1H), 5.47 (d, J=7.44 Hz, 1H), 5.85 (s, 1H), 7.20 (s, 1H), 7.34-7.41 (m, 5H); 13C NMR (CDCl3+CD3OD): δ 54.7, 74.4, 83.0, 104.3, 117.4, 126.7, 127.4, 138.2, 140.6, 149.8, 153.6, 170.7; Analysis: C17H16O5 requires C, 67.99; H, 5.37. found C, 67.92; H, 5.41%.

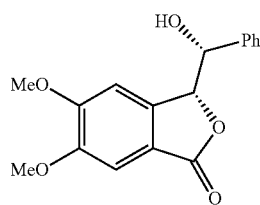

II y

Example 49

(S)-3-((S)-1-Hydroxyethyl)-5,7-dimethoxyisobenzofuran-1(3H)-one (18)

Yield: 93%; colorless solid; mp 139-140° C.; [α]D25+76.89 (c 1.10, CHCl3); IR (CHCl3): 692, 771, 954, 1036, 1063, 1237, 1329, 1361, 1454, 1611, 1725, 2986, 3008, 3447 cm-1; 1H NMR (200 MHz, CDCl3): δ 1.33 (d, J=6.4 Hz, 3H), 2.0 (brs, 1H), 3.88 (s, 3H), 3.94 (s, 3H), 4.09-4.15 (m, 1H), 5.17 (d, J=3.99 Hz, 1H), 6.42 (d, J=1.8 Hz, 1H), 6.52 (d, J=1.8 Hz, 1H); 13C NMR (CDCl3): δ 18.7, 55.9, 68.6, 82.6, 98.3, 99.1, 107.5, 151.9, 159.7, 166.7, 168.0; HRMS (ESI) calcd for: C12H14O5 [M+H]+ 239.0919. found 239.0923.

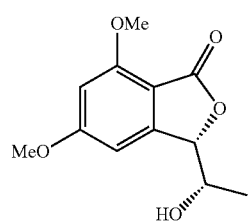

18

Example 50

Preparation of Matteucen C

To a 250 mL RB flask charged with K3Fe(CN)6 (30 mmol), K2CO3 (30 mmol), MeSO2NH2 (10 mmol), tert-BuOH (25 mL), THF (25 mL) and H2O (50 mL). Reaction mixture was stirred for 10 min and (DHQD)2-PHAL (1 mol %) and K2OsO4 (0.5 mol %) were added and stirred for additional 30 min. To the reaction mixture 17 was added and allowed to stir for 6 at 25° C. After completion of reaction, sodium bisulphate (5 g) was added slowly at 0° C. Organic layer was separated and aqueous layer was extracted with ethyl acetate (3×50 ml) combined organic layer was washed with brine (100 mL), dried over sodium sulphate and concentrated under reduced pressure to yield the crude products, Flash column chromatography purification [silica gel (230-400 mesh) and petroleum ether:EtOAc (60:40) as an eluent] afforded 19 in pure form.

To compound 19 was added BBr3 and dichloromethane, stirred till completion of the reaction. After the reaction solid was separated and subjected to reaction to obtain the final product (2a).

(+) Matteucen C (2a). Yield: 68%; colorless powder; [α]D25+54.18 (c 1.0, MeOH); IR (CHCl3): 691, 710, 1169, 1615, 1684, 1725, 3364 cm-1; 1H NMR (500 MHz, DMSO-d6): δ 4.94 (t, J=4.8 Hz, 1H), 5.44 (d, J=4.0 Hz, 1H), 5.72 (d, J=4.8 Hz, 1H), 6.23 (d, J=1.8 Hz, 1H), 6.25 (d, J=1.8 Hz, 1H), 7.24-7.36 (m, 5H), 10.29 (s, 1H), 10.31 (s, 1H); 13C NMR (CDCl3): δ 72.6, 81.7, 101.1, 102.3, 104.2, 126.9, 127.2, 127.6, 140.7, 151.5, 157.6, 163.9, 167.7; HRMS (ESI) calcd for: C15H12O5 [M+H]+ 273.0763. found 273.0766.

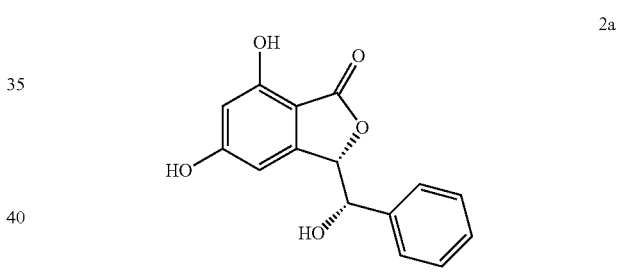

2a

Example 51

3-Butylphthalide (3)

Yield: 86%; Colourless oil; [α]D25−62.1 (c 1.15, CHCl3, ee=99%); lit., 2i [α]D22−62 (c 4.2, CHCl3, ee=99%); IR (CHCl3): 780, 1346, 1465, 1526, 1716, 2932 cm-1; 1H NMR (200 MHz, CDCl3): δ 0.88-0.95 (m, 3H), 1.32-1.53 (m, 4H), 1.68-1.86 (m, 1H), 1.97-2.07 (m, 1H), 5.46 (q, J=7.6 Hz, 1H), 7.42 (dd, J=1.13, 7.6 Hz, 1H), 7.52 (t, J=7.4 Hz, 1H), 7.66 (td, J=1.13, 7.4 Hz, 1H), 7.90 (d, J=7.6 Hz, 1H); 13C NMR (CDCl3): δ 13.9, 22.4, 26.9, 34.4, 81.3, 121.9, 125.5, 129.0, 133.9, 150.1, 170.3; HRMS (ESI) calcd for: C12H14O2[M+H]+ 191.1072. found 191.1069.

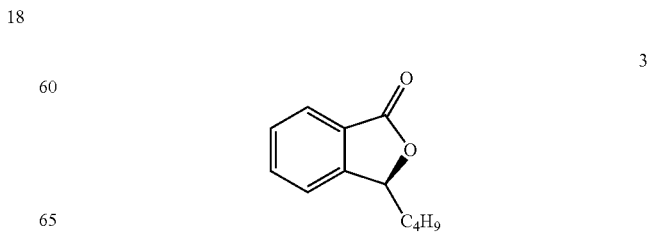

3

Advantages of Present Invention

1. General preparative method that involves a single-step CN-assisted oxidative cyclization leading to synthesis of a wide variety of 3-substituted phthalides and their structural analogues via asymmetric dihydroxylation of o-cyano cinnamates and styrenics.
2. This reaction is highly practical in the sense that the products were obtained in excellent yields (up to 95%) and optical purities (up to 99% ee) in short reaction time and shows broad substrate scope and good functional group tolerance (28 examples).
3. The unusual synergism shown by CN and osmate groups in rate enhancement of asymmetric dihydroxylation process is unique.
4. This method has been successfully demonstrated in the enantioselective synthesis of three natural products namely butylphthalide, demethylpestaphthalide and Matteucen C, thus confirming its structural and stereochemical assignments.
5. The present invention provides a process for preparation of highly biological important phthalides in short reaction time with high yield and high enantioselectivity.

The invention claimed is:

1. A synthesis of compound (3)

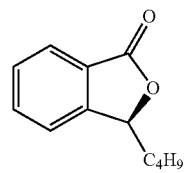

(S)-3-butylisobenzofuran-1(3H)-one comprising (a) reacting an o-cyano substituted aryl alkene of Formula I with AD-mix-β in the presence of a solvent at room temperature ranging between 25-35° C. for a period ranging between 3-7 h

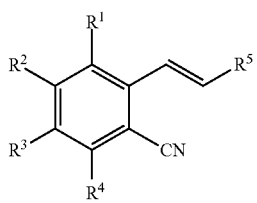

Formula I

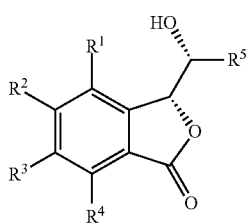

Formula II to form a cyclic amino ether
(b) hydrolyzing the cyclic amino ether with water to form the lactone of Formula II;
wherein AD-mix-β comprises potassium osmate $K_2OsO_2(OH)_4$; potassium ferricyanide $K_3Fe(CN)_6$; potassium carbonate; and chiral ligand $(DHQD)_2PHAL$; and wherein $R_1$, $R_2$, $R_3$ and R4 are hydrogen; and $R_5$ is $C_4H_9$ to form compound (21)

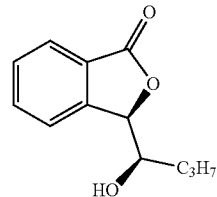

(c) carrying out Barton-Mccombie deoxygenation of compound (21) with 1,1-thiocarbonyl diimidazole in the presence of dichloromethane as solvent at 25-35° C. for 10-14 h followed by treatment with tributyltinhydride in the presence of catalytic amount of azobisisobutyronitrile for 20-40 min to obtain compound (3).

2. A synthesis of compound (2a)

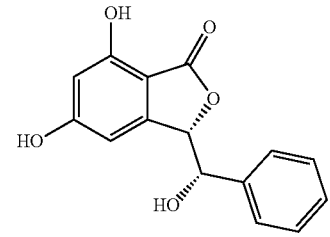

(S)-5,7-dihydroxy-3-((S)-hydroxy(phenyl)methyl)isobenzofuran-1(3H)-one comprising (a) reacting an o-cyano substituted aryl alkene of Formula I with AD-mix-β in the presence of a solvent at room temperature ranging between 25-35° C. for a period ranging between 3-7 h

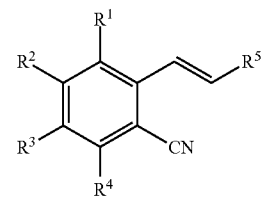

Formula I

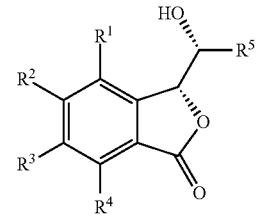

Formula II to form a cyclic amino ether
(b) hydrolyzing the cyclic amino ether with water to form the lactone of Formula II;
wherein AD-mix-β comprises osmate $K_2OsO_2(OH_4)$; potassium ferricyanide $K_3Fe(CN)_6$; potassium carbonate; and chiral ligand $(DHQD)_2PHAL$; and wherein $R_1$ and $R_3$ are hydrogen, $R_2$ and $R_4$ are —OMe, and $R_5$ is unsubstituted phenyl; to form compound (19)

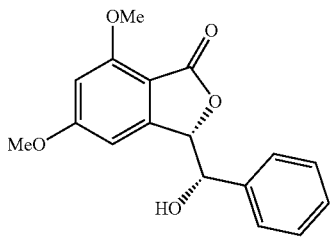

19

(c) adding BBr3 and an organic solvent to compound (19) followed by stirring at 10° C. to 25° C. for 6-8 h to obtain compound (2a).

3. A synthesis of compound (20)

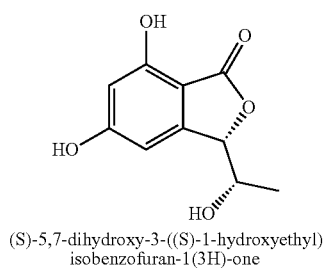

(S)-5,7-dihydroxy-3-((S)-1-hydroxyethyl)isobenzofuran-1(3H)-one comprising (a) reacting an o-cyano substituted aryl alkene of Formula I with AD-mix-β in the presence of a solvent at room temperature ranging between 25-35° C. for a period ranging between 3-7 h

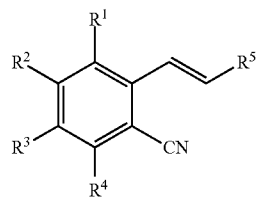

Formula I

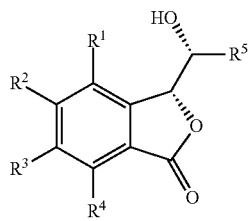

Formula II to form a cyclic amino ether (b) hydrolyzing the cyclic amino ether with water to form the lactone of Formula II;

wherein AD-mix-β comprises potassium osmate $K_2OsO_2(OH)_4$; potassium ferricyanide $K_3Fe(CN)_6$; potassium carbonate; and chiral ligand $(DHQD)_2PHAL$; and wherein $R_1$ and $R_3$ are hydrogen, $R_2$ and R4 are —OMe and $R_5$ is —Me; to form compound (18)

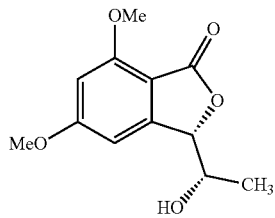

18

(c) adding BBr3 and an organic solvent to compound (18), followed by stirring at 10° C. to 25° C. for 6-8 h to obtain compound (20).

* * * * *